(12) United States Patent
Li et al.

(10) Patent No.: US 11,410,352 B2
(45) Date of Patent: Aug. 9, 2022

(54) SYSTEMS AND METHODS FOR IMAGE RECONSTRUCTION

(71) Applicant: SHANGHAI UNITED IMAGING HEALTHCARE CO., LTD., Shanghai (CN)

(72) Inventors: Cuifang Li, Shanghai (CN); Zheng Zhang, Shanghai (CN); Hushan Chen, Shanghai (CN); Xiaomin Ren, Shanghai (CN); Tianyi Xu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 150 days.

(21) Appl. No.: 17/013,606

(22) Filed: Sep. 6, 2020

(65) Prior Publication Data

US 2021/0074035 A1 Mar. 11, 2021

(30) Foreign Application Priority Data

Sep. 6, 2019 (CN) .......................... 201910844462.4
Apr. 28, 2020 (CN) .......................... 202010350679.2
Apr. 28, 2020 (CN) .......................... 202010369439.7

(51) Int. Cl.
*G06T 11/00* (2006.01)
*A61B 6/03* (2006.01)
*A61B 6/00* (2006.01)

(52) U.S. Cl.
CPC ............ *G06T 11/005* (2013.01); *A61B 6/037* (2013.01); *A61B 6/467* (2013.01); *A61B 6/5247* (2013.01); *G06T 2210/41* (2013.01)

(58) Field of Classification Search
CPC ... G06T 11/005; G06T 2210/41; A61B 6/037; A61B 6/467; A61B 6/5247; A61B 6/4417; A61B 6/5211; A61N 2005/1052; A61N 2005/1055; A61N 2005/1061; A61N 5/1049
See application file for complete search history.

(56) References Cited

U.S. PATENT DOCUMENTS

2021/0106847 A1* 4/2021 Mok .......................... G06T 7/38

* cited by examiner

*Primary Examiner* — Courtney D Thomas
(74) *Attorney, Agent, or Firm* — Metis IP LLC

(57) ABSTRACT

A method may include obtaining a first acquisition time period related to a scan of a first modality performed on an object. The method may also include obtaining one or more second acquisition time periods related to a scan of a second modality performed on the object. The method may also include obtaining, based on the first acquisition time period and the one or more second acquisition time periods, target data of the object acquired in the scan of the first modality. The method may also include generating one or more target images of the object based on the target data.

20 Claims, 13 Drawing Sheets

SYSTEMS AND METHODS FOR IMAGE RECONSTRUCTION

CROSS-REFERENCE TO RELATED APPLICATIONS

This application claims priority of Chinese Patent Application No. 201910844462.4, filed on Sep. 6, 2019, Chinese Patent Application No. 202010350679.2, filed on Apr. 28, 2020, and Chinese Application No. 202010369439.7, filed on Apr. 28, 2020, the contents of each of which are hereby incorporated by reference.

TECHNICAL FIELD

The disclosure generally relates to image processing, and more particularly, to systems and methods for image reconstruction.

BACKGROUND

Emission computed tomography (ECT) is a type of tomography involving radioactive emissions. In ECT, a tracer with radioactivity is introduced into an object (e.g., a patient). After the tracer is metabolized in the object, differences in radioactive concentration of the tracer are formed between diseased parts and normal tissue in the object. One or more images are generated based on the differences through computer processing. The ECT includes positron emission tomography (PET) and single photon emission computed tomography (SPECT).

SUMMARY

In an aspect of the present disclosure, a system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a first acquisition time period related to a scan of a first modality performed on an object. The one or more processors may obtain one or more second acquisition time periods related to a scan of a second modality performed on the object. The one or more processors may obtain, based on the first acquisition time period and the one or more second acquisition time periods, target data of the object acquired in the scan of the first modality. The one or more processors may generate one or more target images of the object based on the target data.

In some embodiments, to obtain, based on the first acquisition time period and the one or more second acquisition time periods, the target data of the object acquired in the scan of the first modality, the one or more processors may determine one or more third acquisition time periods based on the first acquisition time period and the one or more second acquisition time periods. Each of the one or more third acquisition time periods may be consistent with one of the one or more second acquisition time periods. The one or more processors may obtain the target data acquired during the one or more third acquisition time periods in the scan of the first modality.

In some embodiments, the one or more processors may cause at least one of the first acquisition time period, the one or more second acquisition time periods, or the one or more third acquisition time periods to be displayed.

In some embodiments, the one or more processors may store the one or more third acquisition time periods.

In some embodiments, to generate the one or more target images of the object based on the target data, the one or more processors may obtain one or more reconstruction parameters associated with the target data. The one or more processors may generate, based on the target data and the one or more reconstruction parameters, the one or more target images of the object.

In some embodiments, the one or more reconstruction parameters may include at least one of a count of the one or more target images or a frame time of the one or more target images.

In some embodiments, to generate the one or more target images of the object based on the target data, the one or more processors may divide, based on the one or more reconstruction parameters, the target data into one or more imaging data sub-sets. The one or more processors may generate the one or more target images of the object based on the one or more imaging data sub-sets.

In some embodiments, the one or more processors may cause the one or more reconstruction parameters to be displayed.

In some embodiments, the one or more processors may cause to be displayed at least one of an adding button configured to cause the one or more reconstruction parameters of the target data to be added into a list, a deletion button configured to cause the one or more reconstruction parameters to be deleted from the list, a saving button configured to cause the one or more reconstruction parameters to be saved, an export button configured to cause the one or more reconstruction parameters to be exported, an import button configured to cause the one or more reconstruction parameters or the first acquisition time period to be obtained, or a reconstruction button configured to cause the target data to be reconstructed.

In some embodiments, the one or more processors may generate, in real time based on original data having been acquired in the scan of the first modality, an acquisition curve while the scan of the first modality is being performed. The one or more processors may cause the acquisition curve to be displayed.

In some embodiments, the acquisition curve may reflect a temporal variation of a count rate of the original data.

In some embodiments, the first acquisition time period may be obtained based on the acquisition curve.

In some embodiments, to obtain the first acquisition time period related to the scan of the first modality performed on the object, the one or more processors may receive a user instruction related to a user operation performed with respect to the displayed acquisition curve. The one or more processors may obtain the first acquisition time period based on the user instruction.

In some embodiments, the user operation may include at least one of specifying, on the displayed acquisition curve, a start point of the first acquisition time period, an end point of the first acquisition time period, or a duration of the first acquisition time period.

In some embodiments, the one or more processors may cause to be displayed a button configured to cause at least a portion of the acquisition curve to be zoomed in or out.

In some embodiments, the one or more processors may cause to be displayed an injection time of a radioactive tracer into the object in the acquisition curve.

In some embodiments, the first modality may be positron emission tomography (PET) or single photon emission computed tomography (SPECT), and the second modality may be magnetic resonance (MR).

In some embodiments, one or more scan sequences may be applied in the scan of the second modality.

In some embodiments, each of the one or more second acquisition time periods may correspond to one of the one or more scan sequences.

In some embodiments, at least a portion of the scan of the second modality may be performed synchronously with at least a portion of the scan of the first modality.

In some embodiments, the one or more processors may obtain second modality data acquired in at least one of the one or more second acquisition time periods of the scan of the second modality. The at least one of the one or more second acquisition time periods may relate to the first acquisition time period. The one or more processors may generate one or more second modality images of the object based on the second modality data. The one or more processors may cause the one or more target images and the one or more second modality images to be displayed in fusion.

According to another aspect of the present disclosure, a method may include one or more of the following operations. One or more processors may obtain a first acquisition time period related to a scan of a first modality performed on an object. The one or more processors may obtain one or more second acquisition time periods related to a scan of a second modality performed on the object. The one or more processors may obtain, based on the first acquisition time period and the one or more second acquisition time periods, target data of the object acquired in the scan of the first modality. The one or more processors may generate one or more target images of the object based on the target data.

According to yet another aspect of the present disclosure, a system may include a time obtaining module configured to obtain a first acquisition time period related to a scan of a first modality performed on an object, and obtain one or more second acquisition time periods related to a scan of a second modality performed on the object. The system may also include a data obtaining module configured to obtain, based on the first acquisition time period and the one or more second acquisition time periods, target data of the object acquired in the scan of the first modality. The system may also include a reconstruction module configured to generate one or more target images of the object based on the target data.

According to yet another aspect of the present disclosure, a non-transitory computer readable medium may comprise at least one set of instructions. The at least one set of instructions may be executed by one or more processors of a computing device. The one or more processors may obtain a first acquisition time period related to a scan of a first modality performed on an object. The one or more processors may obtain one or more second acquisition time periods related to a scan of a second modality performed on the object. The one or more processors may obtain, based on the first acquisition time period and the one or more second acquisition time periods, target data of the object acquired in the scan of the first modality. The one or more processors may generate one or more target images of the object based on the target data.

According to yet another aspect of the present disclosure, a system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain original data acquired by performing a scan on an object. The one or more processors may generate, in real time based on the original data, an acquisition curve while the scan is being performed. The one or more processors may obtain a reconstruction range based on the acquisition curve. The one or more processors may obtain, from the original data, target data based on the reconstruction range. The one or more processors may generate one or more target images of the object based on the target data.

In some embodiments, the acquisition curve may reflect a temporal variation of a count rate of the original data.

In some embodiments, the one or more processors may cause the acquisition curve to be displayed.

In some embodiments, to obtain the reconstruction range based on the acquisition curve, the one or more processors may receive a user instruction related to a user operation performed with respect to the displayed acquisition curve. The one or more processors may obtain the reconstruction range based on the user instruction.

In some embodiments, the user operation may include at least one of specifying, on the displayed acquisition curve, a start point of the reconstruction range, an end point of the reconstruction range, or a duration of the reconstruction range.

In some embodiments, the one or more processors may cause to be displayed an injection time of a radioactive tracer into the object.

In some embodiments, the one or more processors may cause the reconstruction range to be displayed.

In some embodiments, to generate the one or more target images of the object based on the target data, the one or more processors may obtain one or more reconstruction parameters associated with the target data. The one or more processors may generate, based on the target data and the one or more reconstruction parameters, the one or more target images of the object.

In some embodiments, the one or more reconstruction parameters may include at least one of a count of the one or more target images or a frame time of the one or more target images.

In some embodiments, the one or more processors may cause the one or more reconstruction parameters to be displayed.

In some embodiments, the one or more processors may store at least one of the reconstruction range or the one or more reconstruction parameters.

In some embodiments, the one or more processors may cause to be displayed at least one of an adding button configured to cause the one or more reconstruction parameters of the target data to be added into a list, a deletion button configured to cause the one or more reconstruction parameters to be deleted from the list, a saving button configured to cause the one or more reconstruction parameters to be saved, an export button configured to cause the one or more reconstruction parameters to be exported, an import button configured to cause the one or more reconstruction parameters to be obtained from candidate reconstruction parameters, a zooming button configured to cause at least a portion of the acquisition curve to be zoomed in or out, or a reconstruction button configured to cause the target data to be reconstructed.

In some embodiments, the scan may be a positron emission tomography (PET) scan or a single photon emission computed tomography (SPECT) scan.

According to yet another aspect of the present disclosure, a method may include one or more of the following operations. One or more processors may obtain original data acquired by performing a scan on an object. The one or more processors may generate, in real time based on the original data, an acquisition curve while the scan is being performed. The one or more processors may obtain a reconstruction range based on the acquisition curve. The one or more processors may obtain, from the original data, target data based on the reconstruction range. The one or more processors may generate one or more target images of the object based on the target data.

According to yet another aspect of the present disclosure, a system may include a data obtaining module, a time obtaining module, and a reconstruction module. The data obtaining module is configured to obtain original data acquired by performing a scan on an object. The time obtaining module is configured to generate, in real time based on the original data, an acquisition curve while the scan is being performed, and obtain a reconstruction range based on the acquisition curve. The data obtaining module is configured to obtain, from the original data, target data based on the reconstruction range. The reconstruction module is configured to generate one or more target images of the object based on the target data.

According to yet another aspect of the present disclosure, a non-transitory computer readable medium may comprise at least one set of instructions. The at least one set of instructions may be executed by one or more processors of a computing device. The one or more processors may obtain original data acquired by performing a scan on an object. The one or more processors may generate, in real time based on the original data, an acquisition curve while the scan is being performed. The one or more processors may obtain a reconstruction range based on the acquisition curve. The one or more processors may obtain, from the original data, target data based on the reconstruction range. The one or more processors may generate one or more target images of the object based on the target data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
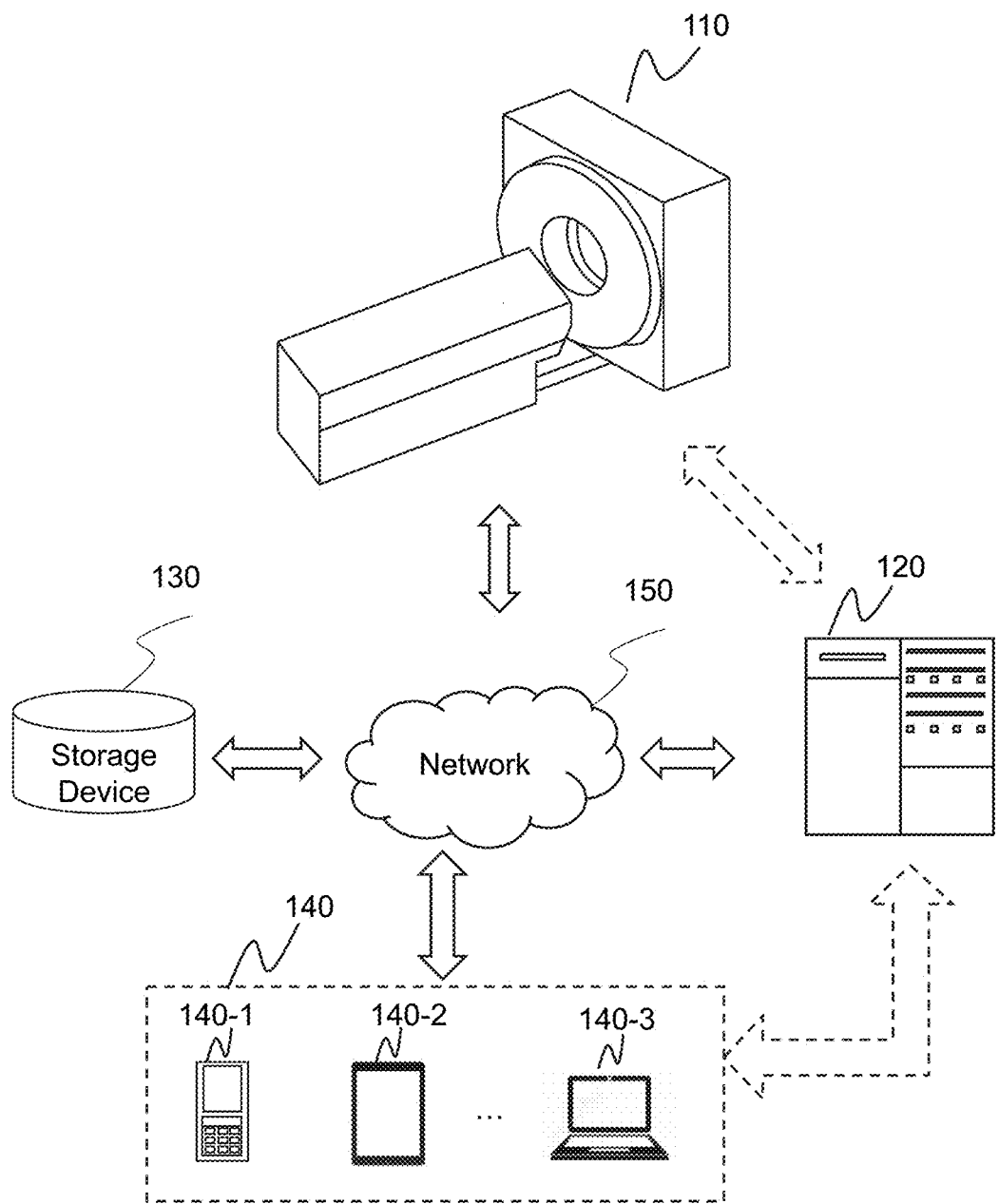
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, "A and/or B" denotes including A, including B, or including A and B. The term "image" in the present disclosure is used to collectively refer to image data (e.g., scan data) and/or images of various forms, including a two-dimensional (2D) image, a three-dimensional (3D) image, a four-dimensional (4D) image, etc. The terms "first," "second," "third," etc. are used to distinguish similar objects and does not denote a specific ranking of the objects. The character "/" includes one of the associated terms.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include an imaging system. The imaging system may include a single-modality system and/or a multi-modality system. The term "modality" used herein broadly refers to an imaging or treatment method or technology that gathers, generates, processes, and/or analyzes imaging information of a subject or treatments the subject. The single-modality system may include, for example, a positron emission tomography (PET) system or a single photon emission computed tomography (SPECT) system. The multi-modality system may include, for example, a positron emission tomography-magnetic resonance imaging (PET-MRI) system, a positron emission tomography-computed tomography (PET-CT) system, a single photon emission computed tomography-magnetic resonance imaging (SPECT-MRI) system, or a single photon emission computed tomography-computed tomography (SPECT-CT) system. It should be noted that the medical system described below is merely provided for illustration purposes, and not intended to limit the scope of the present disclosure.

In some embodiments, the systems may include a treatment system. The treatment system may include a treatment plan system (TPS), image-guided radiotherapy (IGRT) system, etc. The image-guided radiotherapy (IGRT) system may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include a single-modality device and/or a multi-modality device. The single-modality device may include, for example, a PET scanner or an SPECT scanner. The multi-modality device may include, for example, a PET-MRI scanner, a PET-CT scanner, an SPECT-MRI scanner, or an SPECT-CT scanner.

In the present disclosure, the subject may include a biological object and/or a non-biological object. The biological subject may be a human being, an animal, a plant, or a specific portion, organ, and/or tissue thereof. For example, the subject may include a head, a neck, a thorax, a heart, a stomach, a blood vessel, a soft tissue, a tumor, a nodule, or the like, or any combination thereof. In some embodiments, the subject may be a man-made composition of organic and/or inorganic matters that are with or without life. The term "object" or "subject" are used interchangeably in the present disclosure.

In the present disclosure, a representation of an object (e.g., a patient, a subject, or a portion thereof) in an image may be referred to as an object for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as a segmentation of an organ or tissue for brevity.

ECT, such as PET and SPECT, is widely used in disease diagnosis and/or treatment for various medical conditions (e.g., tumors, psychiatric diseases, etc.). During ECT imaging, a radioactive tracer may be injected into a subject (e.g., a patient) to be scanned without changing the physiological state of the subject. For example, in SPECT imaging, a patient may be injected into a tracer emitting gamma photons. As another example, in PET imaging, a patient may be injected into a tracer emitting positrons that combine with electrons in the patient to produce gamma photons. The radioactive tracer may participate in the physiological metabolism of the subject. Then, a PET or SPECT scan may be performed to detect gamma photons emitted from the subject. One or more PET or SPECT images of the subject may be reconstructed based on imaging data including information of the detected gamma photons acquired in the PET or SPECT scan to evaluate the physiology (or functionality) functions of the subject, thereby achieving diagnosis purposes.

In some embodiments, the ECT may be applied together with other imaging types, such as MRI and CT, forming multi-modality imaging. Exemplary multi-modality imaging may include PET-CT, PET-MRI, SPECT-CT, SPECT-MRI, etc. The multi-modality imaging may acquire multi-modality imaging data of a subject and generate one or more multi-modality images of the subject based on the multi-modality imaging data, which can help a user (e.g., a doctor, a technician, an engineer, etc.) to quickly ascertain the anatomical, physiological and metabolic changes of lesions and normal tissue, and provide the user with more abundant information for diagnosis.

In an aspect of the present disclosure, systems and methods for image reconstruction are provided. The systems and methods may obtain original data (e.g., PET data or SPECT data) acquired by performing a scan (e.g., a PET scan or an SPECT can) on an object. The systems and methods may generate, in real time based on the original data, an acquisition curve while the scan is being performed. The systems and methods may obtain an acquisition time period (also referred to as a reconstruction range) based on the real-time acquisition curve. The systems and methods may obtain, from the original data, target data that is acquired during the acquisition time period. The systems and methods may generate one or more target images (e.g., PET images or SPECT images) of the object based on the target data. The systems and the methods allows the process that the acquisition curve develops from the start to the end of the scan to be presented to a user in real-time. The acquisition curve may be adaptively displayed on an interactive interface, such that the displayed acquisition curve may not be too small or too large in the interactive interface, thereby the user can observe the acquisition curve conveniently. The systems and the methods also allows the reconstruction range to be determined and/or adjusted in the acquisition curve that is updated in real-time, so that the reconstruction range may be determined and/or adjusted during the scan is being performed, instead of before or after the scan. The systems and the methods also allows the PET or SPECT reconstruction to be performed during the scan is being performed, instead of after the scan, so that one or more desired PET or SPECT images may be presented to a user before the PET or SPECT scan is finished. Therefore, the interactivity and real-time performance of PET or SPECT may be improved, thereby improving clinical efficiency of PET or SPECT.

Another aspect of the present disclosure relates to systems and methods for image reconstruction in multi-modality imaging (e.g., PET-MRI, or SPECT-MRI). PET-MRI is taken as an example for illustration. One or more MR images may be generated based on an MR scan sequence that is performed in an MR scan. PET data that is acquired in a time period in which the MR scan sequence is performed needs to be obtained to generate one or more PET image so that the one or more MR images and the one or more PET images may be registered and fused accurately. An acquisition time period (also referred to as a reconstruction range) may be determined to obtain the PET data to be reconstructed. If the reconstruction range is not consistent with the time period corresponding to the MR scan sequence, the registration and the fusion of the one or more MR images and the one or more PET images may be inaccurate. Therefore, after the reconstruction range is determined, the systems and/the methods may automatically modify the reconstruction range to be consistent with the time period corresponding to the MR scan sequence. The systems and the methods also allows time periods corresponding to MR scan sequences to be displayed in the coordinate system of the PET acquisition curve, so that a comparison between the process of the PET scan and the process of the MR scan is presented in an interactive interface. A user may determine a PET reconstruction range on the PET acquisition curve using the displayed time periods corresponding to MR scan sequences for reference. The systems and the methods also allows visualized adjustment of a frame count, a frame time, and a PET reconstruction range. The systems and the methods also allows import and export of reconstruction parameters, which may simplify the operation of inputting reconstruction parameters.

FIG. 1 is a schematic diagram illustrating an exemplary imaging system according to some embodiments of the present disclosure. In some embodiments, the imaging system 100 may be a single-modality system (e.g., a PET system, a SPECT system, etc.) or a multi-modality system (e.g., a PET-MRI system, a PET-CT system, an SPECT-MRI system, an SPECT-CT system, etc.).

Merely by way of example, as illustrated in FIG. 1, the imaging system 100 may include an imaging device 110, a processing device 120, a storage device 130, one or more terminals 140, and a network 150. The components in the imaging system 100 may be connected in various ways. Merely by way of example, the imaging device 110 may be connected to the processing device 120 through the network 150 or directly as illustrated in FIG. 1. As another example, the terminal(s) 140 may be connected to the processing device 120 via the network 150 or directly as illustrated in FIG. 1.

The imaging device 110 may be configured to acquire imaging data relating to at least one part of an object. The imaging device 110 may scan the object or a portion thereof that is located within its detection region and generate imaging data relating to the object or the portion thereof. In some embodiments, the imaging data relating to at least one part of an object may include an image (e.g., an image slice), PET data (e.g., gamma photon information), SPECT data (e.g., gamma photon information), magnetic resonance (MR) data (e.g., echo signals), CT data (e.g., projection data), or the like, or a combination thereof. In some embodiments, the imaging data may be two-dimensional (2D) imaging data, three-dimensional (3D) imaging data, four-dimensional (4D) imaging data, or the like, or any combination thereof. In some embodiments, the object may be biological or non-biological. For example, the object may include a patient, a man-made object, etc. As another example, the object may include a specific portion, organ, and/or tissue of the patient. For illustration, the object may include the head, the neck, the thorax, the heart, the stomach, a blood vessel, soft tissue, a tumor, nodules, or the like, or any combination thereof. In some embodiments, the imaging device 110 may include a single-modality imaging device or a multi-modality device. Exemplary single-modality imaging devices may include a PET device, an SPECT device, etc. Exemplary multi-modality devices may include a PET-MRI device, a PET-CT device, an SPECT-MRI device, an SPECT-CT device, etc.

The processing device 120 may process data and/or information obtained from the imaging device 110, the terminal(s) 140, and/or the storage device 130. For example, the processing device 120 may obtain a first acquisition time period related to a scan of a first modality performed on an object and/or one or more second acquisition time periods related to a scan of a second modality performed on the object. The processing device 120 may also obtain, based on the first acquisition time period and the one or more second acquisition time periods, target data of the object acquired in the scan of the first modality. The processing device 120 may generate one or more target images of the object based on the target data. As another example, the processing device 120 may obtain original data acquired by performing a scan of a first modality on an object. The processing device 120 may also generate, in real time based on the original data, an acquisition curve while the scan of the first modality is being performed. The processing device 120 may further obtain a first acquisition time period based on the real-time acquisition curve. In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the imaging device 110, the terminal(s) 140, and/or the storage device 130 via the network 150. As another example, the processing device 120 may be directly connected to the imaging device 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. For example, the storage device 130 may store imaging data (e.g., PET data, SPECT data, MR data, CT data, one or more images) acquired by the imaging device 110. As another example, the storage device 130 may store one or more reconstruction parameters for PET or SPECT reconstruction. As further another example, the storage device 130 may store acquisition time periods related to a scan of the first modality and/or the second modality. In some embodiments, the storage device 130 may store data and/or instructions that the processing device 120 may execute or use to perform exemplary methods/systems described in the present disclosure. For example, the storage device 130 may store data and/or instructions that the processing device 120 may execute or use to modify a first acquisition time period to be consistent with a second acquisition time period in which an MR scan sequence is performed. As another example, the storage device 130 may store data and/or instructions that the processing device 120 may execute or use to generate an acquisition curve when a PET or SPECT scan is being performed. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

In some embodiments, a user (e.g., a doctor, a technician, or an operator) may interact with the imaging system 100 through the terminal (s) 140. For example, an acquisition curve may be displayed on an interface of the terminal 140. The user may perform one or more user operations with respect to the acquisition curve via the terminal 140. As another example, one or more buttons may be displayed on an interface of the terminal 140. The user may perform a user operation with respect to the button(s) to cause the processing device 120 to perform corresponding operations via the terminal 140. In some embodiments, the terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™ a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the imaging device 110, the terminal(s) 140, the processing device 120, the storage device 130, etc., may communicate information and/or data with one or more other components of the imaging system 100 via the network 150. For example, the processing device 120 may obtain imaging data from the imaging device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components.

Figure 2:
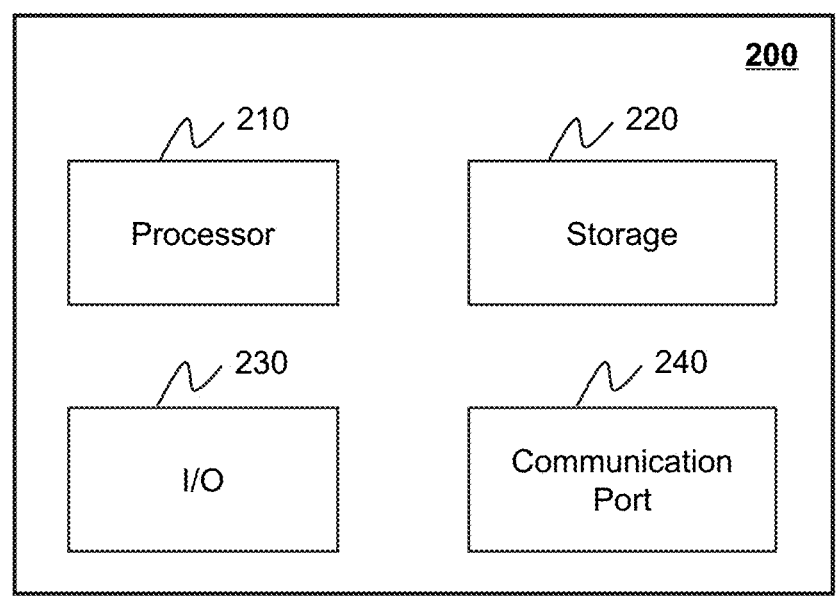
FIG. 2 is a schematic diagram illustrating hardware and/or software components of an exemplary computing device according to some embodiments of the present disclosure.

FIG. 2 is a schematic diagram illustrating hardware and/or software components of an exemplary computing device according to some embodiments of the present disclosure. The computing device 200 may be used to implement any component of the imaging system 100 as described herein. For example, the processing device 120 and/or a terminal 140 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and one or more components (e.g., the imaging device 110, the terminal(s) 140, or the storage device 130) of the imaging system 100, and/or connections between the processing device 120 and one or more external devices (e.g., a database, an external storage, and an image/data processing work station, etc.).

The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

In some embodiments, the components (e.g., the processor 210, the storage 220, the I/O 230, or the communication port 240) of the computing device 200 may be connected and communicate with each other via a bus. The bus may include hardware, software, or the like, or any combination thereof, to couple the components of the computing device 200. The bus may include at least one of a data bus, an address bus, an expansion bus, a local bus. Merely by way of example, the bus may include a graphics bus (e.g., an accelerated graphics port (AGP)), an extended industry standard architecture (EISA) bus, a front side bus (FSB), a hyper transport (HT) interconnect, an industry standard architecture (ISA) bus, an infiniband interconnect, a low pin count (LPC) bus, a storage bus, a micro channel architecture (MCA) bus, a peripheral component interconnect (PCI) bus, a PCI-express (PCI-X) bus, a serial advanced technology attachment (SATA) bus, a video electronics standards association local bus (VLB), or the like, or any combination thereof. In some embodiments, the bus may include one or more buses. The bus may include any type of bus or interconnect, which is not limited herein.

Figure 3:
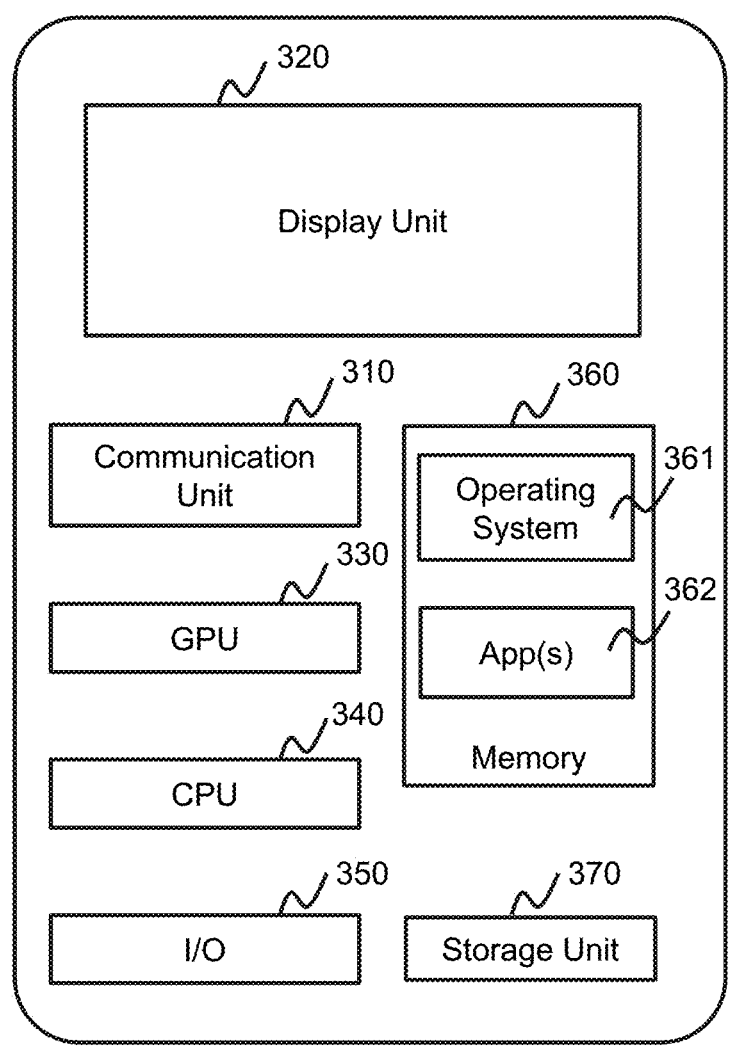
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, one or more components (e.g., a terminal 140 and/or the processing device 120) of the imaging system 100 may be implemented on the mobile device 300.

As illustrated in FIG. 3, the mobile device 300 may include a communication unit 310, a display unit 320, a graphics processing unit (GPU) 330, a central processing unit (CPU) 340, an I/O 350, a memory 360, and a storage unit 370. In some embodiments, any other suitable component, including but not limited to a system bus or a controller (not shown), may also be included in the mobile device 300. In some embodiments, a mobile operating system 361 (e.g., iOS, Android, Windows Phone, etc.) and one or more applications 362 may be loaded into the memory 360 from the storage unit 370 in order to be executed by the CPU 340. The applications 362 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
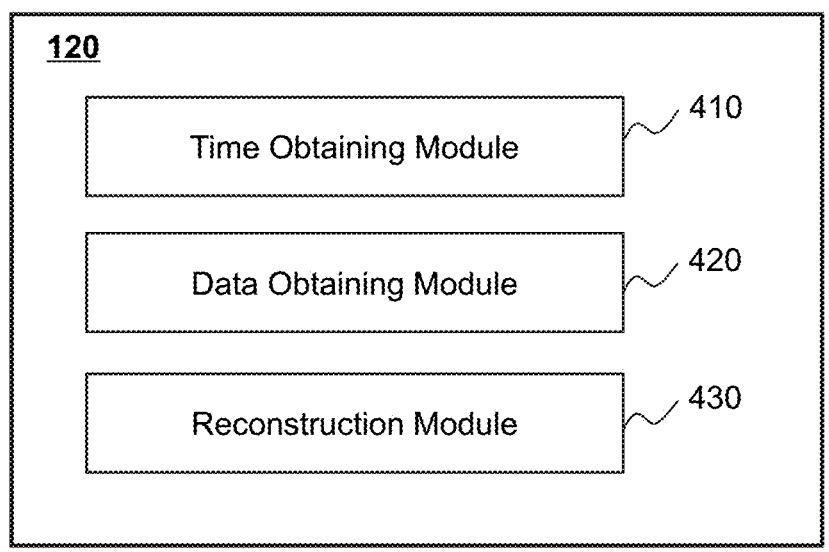
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 120 may include a time obtaining module 410, a data obtaining module 420, and a reconstruction module 430.

The time obtaining module 410 may obtain a first acquisition time period (also referred to as a reconstruction range) related to a scan of a first modality performed on an object. In some embodiments, the time obtaining module 410 may obtain the first acquisition time period based on a user instruction. In some embodiments, the time obtaining module 410 may obtain the first acquisition time period based on a default setting of the imaging system 100. In some embodiments, a plurality of candidate acquisition time periods may be stored in a storage device (e.g., the storage device 130, the storage 220 of the processing device 120, the storage unit 370 of the terminal 140, the memory of the terminal 140, an external storage device, etc.). The time obtaining module 410 or the user may select one of the plurality of candidate acquisition time periods as the first acquisition time period. In some embodiments, the time obtaining module 410 may automatically determine the first acquisition time period.

The data obtaining module 420 may obtain original data acquired by performing a scan (e.g., a PET scan or an SPECT scan) on an object. In some embodiments, the scan may be a single-modality scan or a portion of a multi-modality scan.

The time obtaining module 410 may generate, in real time based on the original data (e.g., PET data or SPECT data), an acquisition curve while the scan is being performed.

In some embodiments, the acquisition curve may reflect a temporal variation of the original data acquired during the scan. For example, the acquisition curve may reflect a temporal variation of a count rate of the original data acquired in the scan. The count rate may refer to a count of gamma protons that are generated based on the tracer, emit from the object, and are detected by the imaging device 110. The horizontal axis of the acquisition time period may denote the time of the scan. The vertical axis of the acquisition time period may denote the count rate of the original data.

In some embodiments, the time obtaining module 410 may determine, based on the original data, a count rate of the original data. The time obtaining module 410 may determine the acquisition curve based on the count rate of the original data. In some embodiments, during the scan, the imaging device 110 may continuously acquire the original data in real time. The time obtaining module 410 may update the acquisition curve based on the real-time updated original data.

The time obtaining module 410 may cause the acquisition curve to be displayed. In some embodiments, the acquisition curve updated in real time may be displayed on an interactive interface through, e.g., the I/O 230 of the processing device 120, and/or the I/O 350 and/or the display unit 320 of the terminal 140, so that the process that the acquisition curve develops from the start to the end of the scan may be presented to a user.

The time obtaining module 410 may obtain one or more second acquisition time periods related to a scan of a second modality on the object. In some embodiments, each of the one or more second acquisition time periods may correspond to one of one or more scan sequences applied in the scan of the second modality. A second acquisition time period may be a portion of the duration of the scan of the second modality.

The time obtaining module 410 may obtain one or more third acquisition time periods based on the first acquisition time period and the one or more second acquisition time periods. In some embodiments, the start point and the end point of each of the one or more third acquisition time periods may be consistent with those of one of the one or more second acquisition time periods. In some embodiments, the time obtaining module 410 may obtain the one or more third acquisition time periods by modifying the first acquisition time period to be consistent with at least one of the one or more second acquisition time periods.

The data obtaining module 420 may obtain, from the original data based on the one or more third acquisition time periods or the first acquisition time period, target data of the object acquired in the scan of the first modality. In some embodiments, the target data of the object may be PET data or SPECT data acquired during the one or more third acquisition time periods or the first acquisition time period. In some embodiments, the target data may include one or more imaging data sets each of which is acquired during one of the one or more third acquisition time periods. In some embodiments, the data obtaining module 420 may obtain the target data from a storage device (e.g., the storage device 130, the storage 220 of the processing device 120, etc.) and/or the imaging device 110.

The reconstruction module 430 may generate one or more target images of the object based on the target data. In some embodiments, a target image may be a PET image or an SPECT image. In some embodiments, for one of the one or more imaging data sets, the reconstruction module 430 may generate a single target image by performing a static reconstruction or generate two or more target images by performing a dynamic reconstruction. In some embodiments, the static reconstruction may be performed when a physiological metabolism of the object and/or a binding of the tracer to tissues of the object are stable after the tracer is injected into the object for a time period (e.g., 0.5 h, 1 h, 2 h, 3 h, etc.). The resultant single target image may evaluate a standard uptake value (SUV) of the tracer in the object quantitatively.

In some embodiments, in the dynamic reconstruction, the imaging data set of the target data may be divided into two or more imaging data sub-sets based on one or more reconstruction parameters. The one or more reconstruction parameters may include the corresponding third acquisition time period and/or frame configuration information. The frame configuration information may include a frame count of the two or more target images to be generated based on the imaging data set and/or a frame time of the two or more target images to be generated. In some embodiments, the reconstruction module 430 may divide, based on the frame count, the imaging data set into two or more imaging data sub-sets. The number (or count) of the two or more imaging data sub-sets may be equal to the frame count. The time period corresponding to each of the two or more imaging data sub-sets may be the same and referred to as the frame time of the two or more target images. The reconstruction module 430 may generate a target image based on each of the two or more imaging data sub-sets. The two or more target images may consist of a dynamic image. The dynamic image may indicate a temporal variation, during one of the one or more third acquisition time period, of activity of the tracer in the object and/or a distribution of the tracer in the object (e.g., tissue of a human body), which can assess a rate value of the physiological metabolism or the binding in vivo quantitatively to reflect a healthy level of target tissue (e.g., a lesion such as a tumor) of the object.

In some embodiments, the data obtaining module 420 may obtain second modality data (e.g., MR data) of the object acquired in the one or more third acquisition time periods. The reconstruction module 430 may generate one or more second modality images (e.g., MR images) based on the second modality data. The reconstruction module 430 may register the one or more target images of the object and the one or more second modality images of the object and cause the one or more target images and the one or more second modality images to be displayed in fusion through, e.g., the I/O 230 of the processing device 120 and/or the display unit 320 of the terminal 140.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media. In some embodiments, the processing device 120 may include one or more additional modules, such as a storage module (not shown) for storing data. In some embodiments, one or more modules of the processing device 120 may be omitted. In some embodiments, two or more modules of the processing device 120 may be integrated into a single module.

Figure 5A:
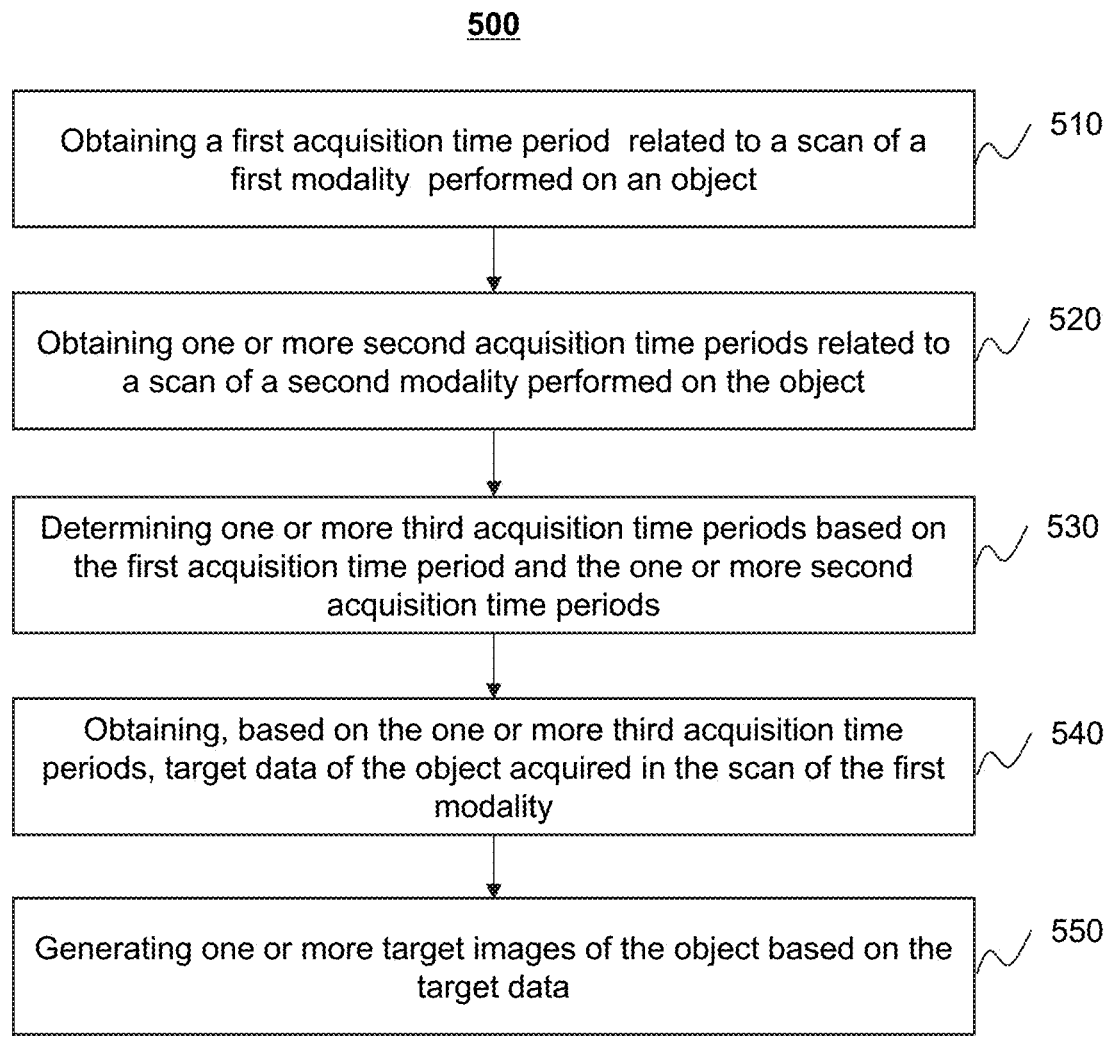
FIG. 5A is a flowchart illustrating an exemplary process for image reconstruction according to some embodiments of the present disclosure.

FIG. 5A is a flowchart illustrating an exemplary process for image reconstruction according to some embodiments of the present disclosure. In some embodiments, process 500 may be implemented as a set of instructions (e.g., an application) stored in a storage device (e.g., the storage device 130 and/or the storage 220 of the processing device 120). The processing device 120 (e.g., the processor 210 and/or one or more modules illustrated in FIG. 4) may execute the set of instructions, and when executing the instructions, the processing device 120 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5A and described below is not intended to be limiting.

In some embodiments, the process 500 may be applied to a multi-modality scan performed by a multi-modality device (e.g., the imaging device 110).

In 510, the processing device 120 (e.g., the time obtaining module 410) may obtain a first acquisition time period (also referred to as a reconstruction range) related to a scan of a first modality performed on an object.

In some embodiments, the scan of the first modality may be a portion of a multi-modality scan (e.g., a PET-MRI scan or an SPECT-MRI scan) performed by a multi-modality device (e.g., the imaging device 110 that is a PET-MRI device or an SPECT-MRI device). In some embodiments, the scan of the first modality may be performed by a first modality component (e.g., a PET component or an SPECT component) of the imaging device 110. In some embodiments, the scan of the first modality may include a PET scan or an SPECT scan. In some embodiments, the first acquisition time period may include at least a portion of the duration of the scan of the first modality.

In some embodiments, before a SPECT scan, the object may be injected into a tracer emitting gamma photons. Alternatively, before a PET scan, the object may be injected into a tracer emitting positrons that combine with electrons in the object to produce gamma photons. During the scan of the first modality, the imaging device 110 may acquire original data (also referred to as first modality data) (e.g., PET data or SPECT data). For example, the original data may include information of gamma photons that emit from the object and are detected by the imaging device 110. The original data may be used to generate one or more first modality images (e.g., PET images or SPECT images) of the object.

In some embodiments, the injection time of the tracer may be determined as the start time of the scan of the first modality. In some embodiments, a time point before or after the injection time of the tracer may be determined as the start time of the scan of the first modality.

In some embodiments, the processing device 120 may obtain the first acquisition time period based on a user instruction. In some embodiments, the processing device 120 may obtain the user instruction based on a user's input operation of the first acquisition time period in an interactive interface through, e.g., the I/O 230 of the processing device 120, the I/O 350 of the terminal 140, and/or the display unit 320 of the terminal 140. For example, the user may input a start time and an end time of the first acquisition time period. As another example, the user may input the duration of the first acquisition time period, and a start time or an end time of the first acquisition time period. In some embodiments, the user may type the first acquisition time period, such as the start time, the end time, or the duration of the first acquisition time period.

In some embodiments, the processing device 120 may generate, based on the original data, an acquisition curve of the scan of the first modality and cause the acquisition curve to be displayed in the interactive interface. The acquisition curve may reflect a temporal variation of the original data acquired during the scan of the first modality. For example, the acquisition curve may reflect a temporal variation of a count rate of the original data acquired in the scan of the first modality. The count rate may refer to a count of gamma photons detected by the imaging device 110 per unit time (e.g., per second). In some embodiments, the processing device 120 may generate the acquisition curve after the scan of the first modality is finished. In some embodiments, the processing device 120 may generate the acquisition curve in real time during the scan of the first modality is being performed. Details regarding real-time generation and display of the acquisition curve may be found elsewhere in the present disclosure (e.g., description in connection with the process 600 in FIG. 6).

In some embodiments, a user (e.g., a doctor, a technician, or an engineering, etc.) may input the first acquisition time period in the displayed acquisition curve. More descriptions regarding inputting the first acquisition time period based on the acquisition curve may be found elsewhere in the present disclosure (e.g., FIGS. 5C-5E and FIGS. 6-7, and the descriptions thereof).

In some embodiments, the processing device 120 may obtain the first acquisition time period based on a default setting of the imaging system 100. For example, the default setting of the first acquisition time period of the imaging system 100 may be the second 5 minutes of the scan of the first modality. As another example, the default setting of the first acquisition time period of the imaging system 100 may be the second ¼ of the scan of the first modality.

In some embodiments, a plurality of candidate acquisition time periods may be stored in a storage device (e.g., the storage device 130, the storage 220 of the processing device 120, the storage unit 370 of the terminal 140, the memory of the terminal 140, an external storage device, etc.). The processing device 120 or the user may select one of the plurality of candidate acquisition time periods as the first acquisition time period.

In some embodiments, the processing device 120 may automatically determine the first acquisition time period based on, e.g., the duration of the scan of the first modality, the position of the object in the detection region of the imaging device 110, the type and concentrate of the tracer, the type of the object, the purpose of scanning the object, the scan protocol used in the multi-modality scan, a reconstruction algorithm, a count of first modality images to be generated, a frame time of the first modality images to be generated, or the like, or any combination thereof.

In 520, the processing device 120 (e.g., the time obtaining module 410) may obtain one or more second acquisition time periods related to a scan of a second modality on the object.

In some embodiments, the scan of the second modality may be a portion of the multi-modality scan. In some embodiments, the scan of the second modality may be performed by an MRI component of the imaging device 110. In some embodiments, the scan of the second modality may include an MR scan.

In some embodiments, the scan of the first modality may be started synchronously with the scan of the second modality. For example, after a tracer is injected into the object for a time period (e.g., 0.5 h, 1 h, 2 h, 3 h, etc.) or immediately after the tracer is injected into the object, the scan of the first modality may be started synchronously with the scan of the second modality.

In some embodiments, the duration of the scan of the first modality or the duration of the scan of the second modality may be equal to or shorter than the duration of the multi-modality scan. In some embodiments, the duration of the scan of the first modality may be equal to or different from the scan of the second modality.

In some embodiments, during the scan of the second modality, one or more scan sequences may be applied consecutively. The one or more scan sequences may include, e.g., an MR based attenuation correction (MRAC) sequence, a fast spin echo (FSE) sequence, a gradient echo (GRE) sequence, a T1-weighted imaging (T1WI) sequence, a T2-weighted imaging (T2WI) sequence, a diffusion-weighted imaging (DWI) sequence, a fluid attenuated inversion recovery (FLAIR) sequence, a diffusion tensor imaging (DTI) sequence, an MR spectroscopy (MRS) sequence, a double inversion recovery (DIR) sequence, a blood oxygen level dependent (BOLD) sequence, or the like. In some embodiments, each of the one or more second acquisition time periods may correspond to one of the one or more scan sequences applied in the scan of the second modality. A second acquisition time period may be a portion of the duration of the scan of the second modality.

In some embodiments, if the one or more second acquisition time periods include multiple second acquisition time periods, there may be no interval between any two neighboring second acquisition time periods of the multiple second acquisition time periods so that the multiple second acquisition time periods may consist of a continuous time period; alternatively, there may be an interval between at least one pair of neighboring second acquisition time periods of the multiple second acquisition time periods so that the multiple second acquisition time periods may consist of one or more discrete time periods. For example, a second scan sequence may be applied after a first scan sequence is finished for a time period equal to the interval. In some embodiments, the intervals of different pairs of neighboring second acquisition time periods of the multiple second acquisition time periods may be the same or different.

In some embodiments, when performing the scan of the second modality, the imaging device 110 may record the time periods for performing the one or more scan sequences. The recorded time periods of the one or more scan sequences may be stored in a storage device (e.g., the storage device 130, the storage 220 of the processing device 120, etc.). The processing device 120 may obtain the one or more second acquisition time periods from the imaging device 110 (e.g., the MRI component of the imaging device 110) or the storage device. In some embodiments, the one or more second acquisition time periods for performing the one or more scan sequences may be preset in, e.g., an MR protocol. The processing device 120 may obtain the one or more second time periods from the MR scan protocol.

Figure 5B:
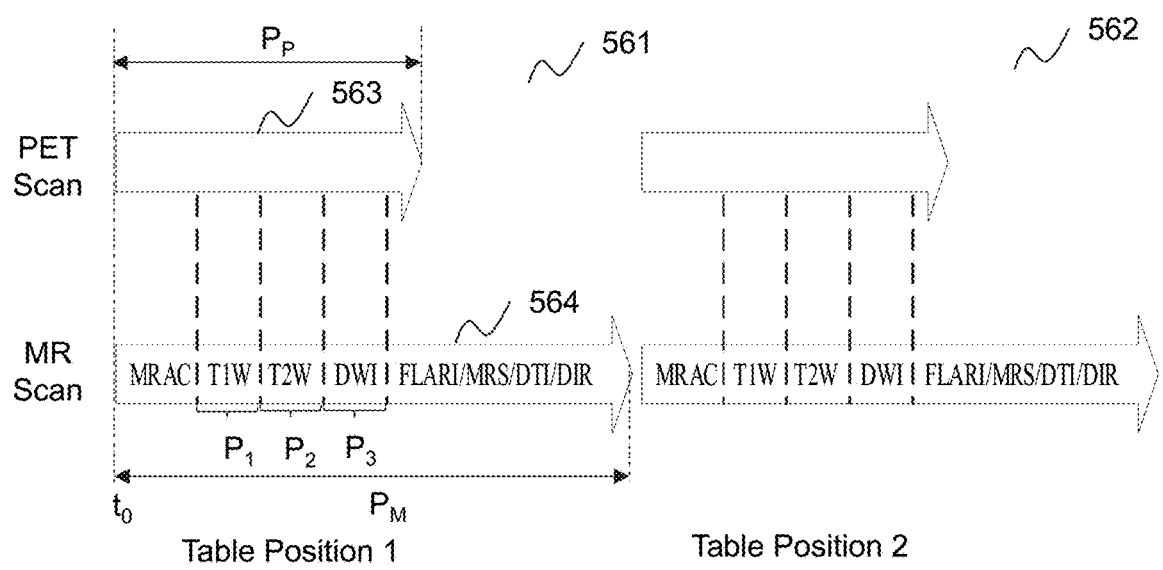
FIG. 5B is a schematic diagram illustrating an exemplary PET-MRI scan according to some embodiments of the present disclosure.

For example, FIG. 5B is a schematic diagram illustrating an exemplary PET-MRI scan according to some embodiments of the present disclosure. In FIG. 5B, the imaging device 110 that is a PET-MRI device is taken as an example for illustration. In some embodiments, an object may be positioned at different positions (also referred to as table positions) in the detection region of the imaging device 110. At one of the different table positions, the imaging device 110 may perform a PET-MRI scan on the object. As shown in FIG. 5B, the imaging device 110 may perform a PET-MRI scan 561 on the object positioned at table position 1. Then, the imaging device 110 may perform a PET-MRI scan 562 on the object positioned at table position 2. For brevity, the PET-MRI scan 561 is taken as an example for illustration.

As shown in FIG. 5B, the PET-MRI scan 561 includes a PET scan 563 and an MR scan 564. The PET scan 563 may be performed by a PET component of the imaging device 110. The MR scan 564 may be performed by an MRI component of the imaging device 110. The PET scan 563 is started synchronously with the MR scan 564 at the time point $t_0$. The duration $P_P$ of the PET scan 563 is shorter than the duration $P_M$ of the MR scan 564. During the MR scan 564, the MRI component performs, in turn, an MRAC sequence, a T1WI sequence, a T2WI sequence, a DWI sequence, a FLAIR sequence, an MRS sequence, a DTI sequence, and a DIR sequence. Merely by way of example, the second acquisition time periods corresponding to the T1 WI sequence, the T2WI sequence, and the DWI sequence may be $P_1$, $P_2$, and $P_3$, respectively. Each of $P_1$, $P_2$, and $P_3$ is a portion of the duration $P_M$ of the MR scan 564. In some embodiments, the scan sequences performed in the PET-MRI scan 561 may be the same as or different from those performed in the PET-MRI 562.

In 530, the processing device 120 (e.g., the time obtaining module 410) may obtain one or more third acquisition time periods based on the first acquisition time period and the one or more second acquisition time periods. In some embodiments, the start point and the end point of each of the one or more third acquisition time periods may be consistent with those of one of the one or more second acquisition time periods. In some embodiments, the processing device 120 may obtain the one or more third acquisition time periods by modifying the first acquisition time period to be consistent with at least one of the one or more second acquisition time periods.

In some embodiments, one or more second modality images (e.g., MR images) may be generated based on MR data (e.g., echo signals) acquired in one of the one or more second acquisition time periods corresponding to one of the one or more scan sequences. At least a portion of the original data corresponding to the second acquisition time period needs to be obtained to generate one or more first modality images (e.g., PET images or SPECT images) so that the one or more MR images and the one or more first modality images may be registered and fused accurately. The first acquisition time period may be used to obtain the at least portion of the original data. If the first acquisition time period is not consistent with the second acquisition time period, the registration and the fusion of the one or more MR images and the one or more first modality images may be inaccurate. Therefore, the processing device 120 may modify the first acquisition time period to the one or more third acquisition time periods each of which is consistent with one of the one or more second acquisition time periods.

In some embodiments, the processing device 120 may determine the one or more third acquisition time periods by modifying the first acquisition time period using an adaptive matching process. The adaptive matching process may refer to a process for modifying the first time period to the one or more third acquisition time periods each of which is consistent with one of the one or more second acquisition time periods.

In some embodiments, the processing device 120 may compare a start point of the first acquisition time period with a start point of at least one of the one or more second acquisition time periods. For example, the processing device 120 may compare the start point of the first acquisition time period with a start point of each of the one or more second acquisition time periods. As another example, if the processing device 120 determines that the start point of the first acquisition time period is within one of the one or more second acquisition time periods (also referred to as a target time period), the processing device 120 may compare the start point of the first acquisition time period with a start point of at least one of the target time period, the second acquisition time period immediately after the target time period, and the second acquisition time period immediately prior to the target time period. As still another example, if the processing device 120 determines that the start point of the first acquisition time period is within an interval between two neighboring second acquisition time periods, the processing device 120 may compare the start point of the first acquisition time period with a start point of at least one of the two neighboring second acquisition time periods. In some embodiments, the processing device 120 may select one of the at least one compared start point and modify the start point of the first acquisition time point to the selected start point. In some embodiments, the selected start point may be closest to the start point of the first acquisition time period among the at least one comparted start point.

In some embodiments, the processing device 120 may compare an end point of the first acquisition time period with an end point of at least one of the one or more second acquisition time periods. For example, the processing device 120 may compare the end point of the first acquisition time period with an end point of each of the one or more second acquisition time periods. As another example, if the processing device 120 determines that the end point of the first acquisition time period is within one of the one or more second acquisition time periods (also referred to as a target time period), the processing device 120 may compare the end point of the first acquisition time period with an end point of at least one of the target time period, the second acquisition time period immediately after the target time period, and the second acquisition time period immediately prior to the target time period. As still another example, if the processing device 120 determines that the end point of the first acquisition time period is within an interval between two neighboring second acquisition time periods, the processing device 120 may compare the end point of the first acquisition time period with an end point of at least one of the two neighboring second acquisition time periods. In some embodiments, the processing device 120 may select one of the at least one compared end point and modify the end point of the first acquisition time point to the selected end point. In some embodiments, the selected end point may be closest to the end point of the first acquisition time period among the at least one comparted end point.

In some embodiments, after modifying the start point and the end point of the first acquisition time period, in response to determining that the modified first acquisition time period includes only one of the one or more second acquisition time periods, the processing device 120 may determine the modified first acquisition time period as a third acquisition time period; and in response to determining that the modified first acquisition time period includes at least two of the one or more second acquisition time periods, the processing device 120 may divide the modified first acquisition time period into at least two third acquisition time periods each of which is consistent with one of the at least two of the one or more second acquisition time periods.

Merely by way of example, the one or more second acquisition time periods may include three time periods denoted by $[t_{11}, t_{12}]$, $[t_{21}, t_{22}]$, and $[t_{31}, t_{32}]$. The first acquisition time period may be denoted by $[t_{41}, t_{42}]$. The processing device 120 may determine one or more third acquisition time periods by modifying $t_{41}$ to one of $t_{11}$, $t_{21}$, and $t_{31}$ which is closest to $t_{41}$ and modifying $t_{42}$ to one of $t_{12}$, $t_{22}$, and $t_{34}$ which is closest to $t_{42}$. The one or more third acquisition time periods may include one time period (e.g., $[t_{11}, t_{12}]$, $[t_{21}, t_{22}]$, or $[t_{31}, t_{32}]$), two time periods (e.g., $[t_{21}, t_{22}]$ and $[t_{31}, t_{32}]$, or $[t_{11}, t_{12}]$ and $[t_{21}, t_{22}]$), or three time periods (e.g., $[t_{11}, t_{12}]$, $[t_{21}, t_{22}]$, and $[t_{31}, t_{32}]$). For example, if $[t_{41}, t_{42}]$ is within $[t_{21}, t_{22}]$, the processing device 120 may determine a third acquisition time period by modifying, based on the adaptive matching process, $[t_{41}, t_{42}]$ to $[t_{21}, t_{22}]$.

In 540, the processing device 120 (e.g., the data obtaining module 420) may obtain, from the original data based on the one or more third acquisition time periods, target data of the object acquired in the scan of the first modality.

In some embodiments, the target data of the object may be the first modality data (e.g., PET data or SPECT data) acquired during the one or more third acquisition time periods in the scan of the first modality. In some embodiments, the target data may include one or more imaging data sets each of which is acquired during one of the one or more third acquisition time periods. In some embodiments, the processing device 120 may obtain the target data from a storage device (e.g., the storage device 130, the storage 220 of the processing device 120, etc.) and/or the imaging device 110.

In 550, the processing device 120 (e.g., the reconstruction module 430) may generate one or more target images of the object based on the target data. In some embodiments, a target image may be a first modality image, such as a PET image or an SPECT image.

In some embodiments, for one of the one or more imaging data sets, the processing device 120 may generate a single target image by performing a static reconstruction or generate two or more target images by performing a dynamic reconstruction. In some embodiments, the static reconstruction may be performed when a physiological metabolism of the object and/or a binding of the tracer to tissues of the object are stable after the tracer is injected into the object for a time period (e.g., 0.5 h, 1 h, 2 h, 3 h, etc.). The resultant single target image may evaluate a standard uptake value (SUV) of the tracer in the object quantitatively.

In some embodiments, in the dynamic reconstruction, the imaging data set of the target data may be divided into two or more imaging data sub-sets based on one or more reconstruction parameters. The one or more reconstruction parameters may include the corresponding third acquisition time period and/or frame configuration information. The frame configuration information may include a frame count of the two or more target images to be generated based on the imaging data set and/or a frame time of the two or more target images to be generated. In some embodiments, the processing device 120 may divide, based on the frame count, the imaging data set into two or more imaging data sub-sets. The number (or count) of the two or more imaging data sub-sets may be equal to the frame count. The time period corresponding to each of the two or more imaging data sub-sets may be the same and referred to as the frame time of the two or more target images. The processing device 120 may generate a target image based on each of the two or more imaging data sub-sets. The two or more target images may consist of a dynamic image. The dynamic image may indicate a temporal variation, during one of the one or more third acquisition time period, of activity of the tracer in the object and/or a distribution of the tracer in the object (e.g., tissue of a human body), which can assess a rate value of the physiological metabolism or the binding in vivo quantitatively to reflect a healthy level of target tissue (e.g., a lesion such as a tumor) of the object. More descriptions regarding the generation of the two or more target images based on the one or more reconstruction parameters may be found elsewhere in the present disclosure (e.g., FIG. 8 and the descriptions thereof).

In some embodiments, the processing device 120 may obtain second modality data (e.g., MR data) of the object acquired in the one or more third acquisition time periods. The processing device 120 may generate one or more second modality images (e.g., MR images) based on the second modality data. The processing device 120 may register the one or more target images of the object and the one or more second modality images of the object and cause the one or more target images and the one or more second modality images to be displayed in fusion through, e.g., the I/O 230 of the processing device 120 and/or the display unit 320 of the terminal 140.

In some embodiments, according to the process 500, the time period of PET or SPECT image reconstruction may be consistent with an MR scan sequence acquisition time period. The start time and the end time of the PET or SPECT reconstruction time range may be consistent with those of the MR reconstruction time range so that the PET or SPECT data used to generate PET or SPECT images and the MR data that is generated based on an MR scan sequence and used to generate MR images are acquired during the same period of time. The PET or SPECT data and the MR data acquired during the same period of time may represent completely consistent physiological activities, so that the resultant PET or SPECT images and MR images may be better registered and fused. The process 500 may be used in the scanning of the nervous system or blood vessels in the head, liver, heart, prostate and other parts. By analyzing the results of accurate registration and fusion of PET (or SPECT) and MR images, from the molecular level, the study of physiological and biochemical processes such as metabolism, blood flow, receptor characteristics, gene expression, etc. of tissues and organs may provide doctors with a wealth of anatomical, physiological, and functional metabolism information.

In some embodiments, the process 500 for imaging reconstruction may be applied in scenarios including: brain science research, brain tumor dynamic imaging, liver dynamic imaging, cardiac dynamic imaging, prostate dynamic imaging, new drug research (e.g., including continuous PET dynamic reconstruction with different time resolutions), PET imaging data (e.g., related to head, neck, chest, abdomen, pelvic cavity, heart, breast, etc.) cropping, PET (or SPECT)/MR synchronous dynamic scanning (e.g., including selecting a certain section of PET data to perform dynamic reconstruction), etc. The PET imaging data cropping may include cropping PET imaging data based on a start time and an end time of an MR scan sequence.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 500 may be omitted and/or one or more additional operations may be added. For example, a storing operation may be added elsewhere in the process 500. In the storing operation, the processing device 120 may store information and/or data (e.g., the reconstruction parameters and/or the one or more target images) generated in the process 500 in a storage device (e.g., the storage device 130, the storage 220 of the processing device 120, the storage unit 370 of the terminal 140, the memory of the terminal 140, an external storage device, etc.).

Figure 5C:
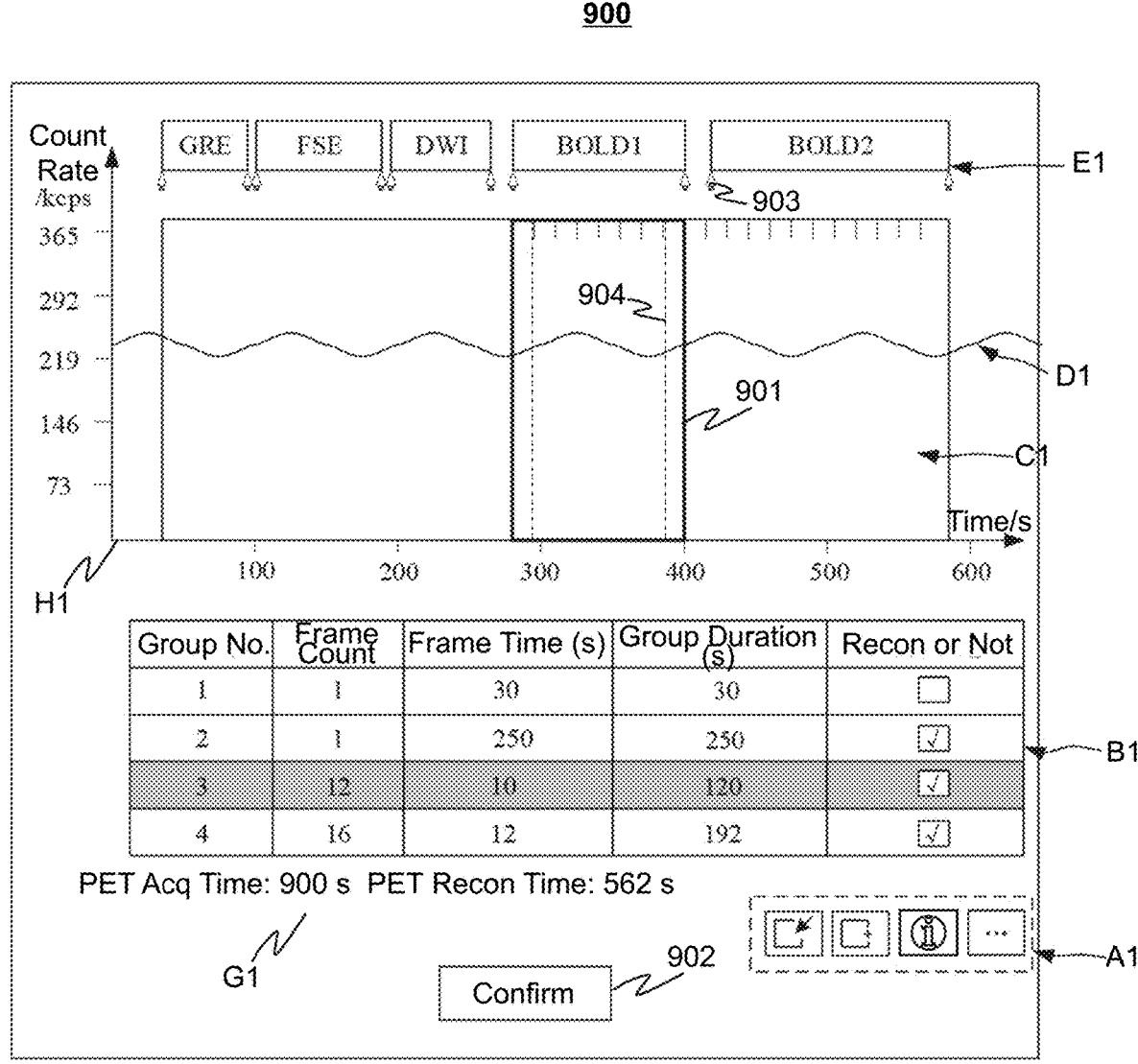
FIGS. 5C-5E are schematic diagrams illustrating exemplary interactive interfaces each of which corresponds to a PET-MRI scan according to some embodiments of the present disclosure.
Figure 5D:
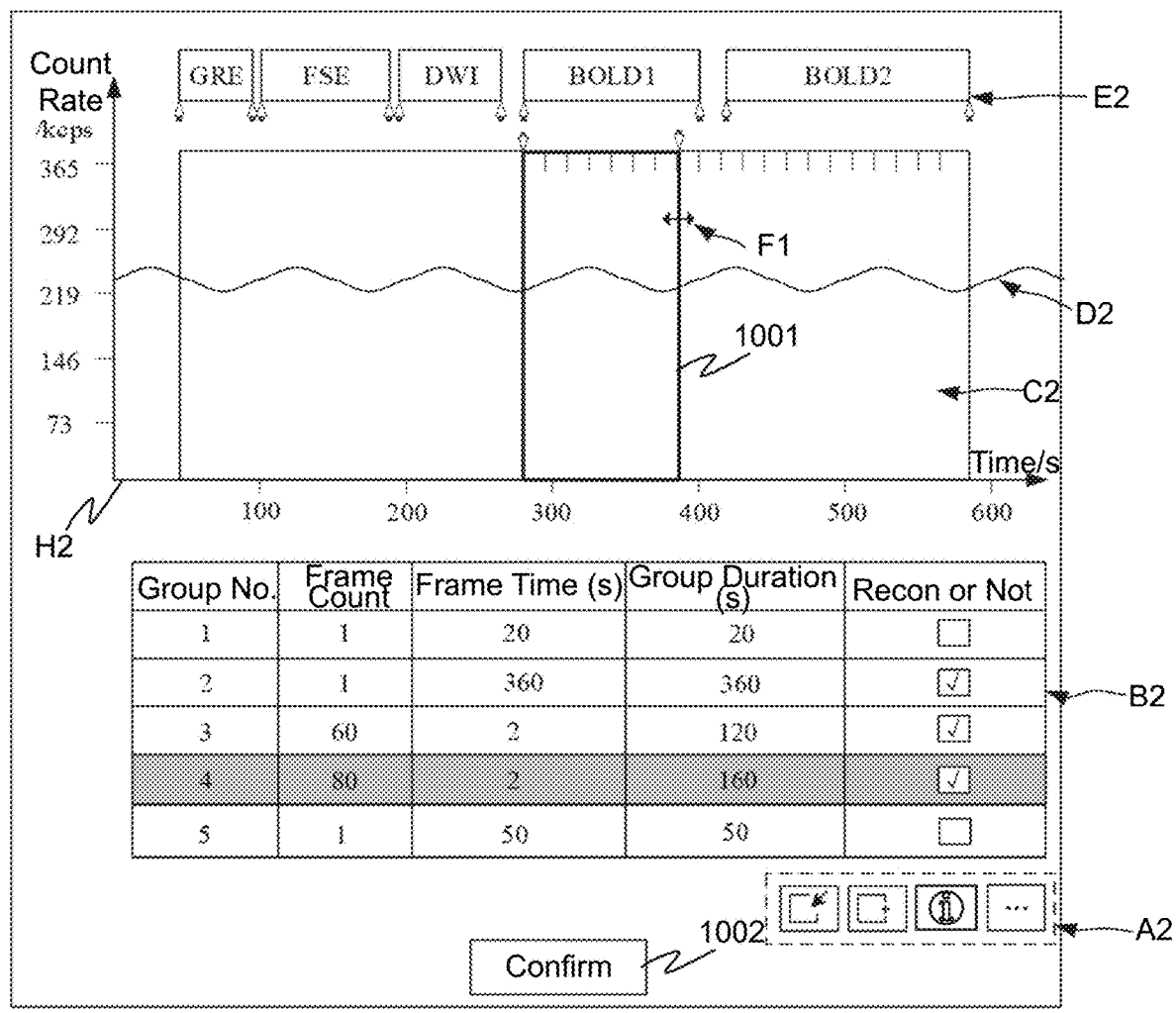
Figure 5E:
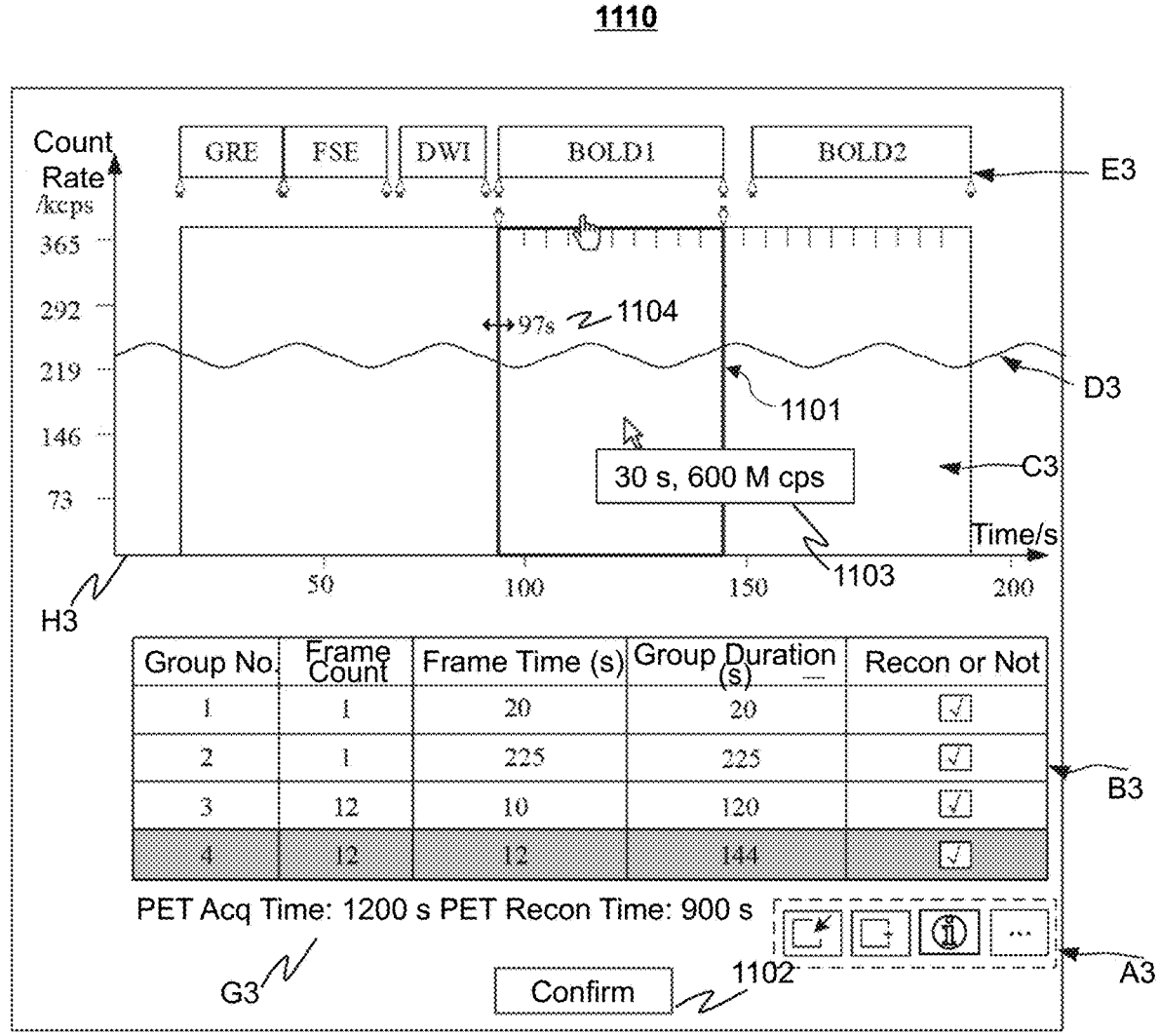

FIGS. 5C-5E are schematic diagrams illustrating exemplary interactive interfaces each of which corresponds to a PET-MRI scan according to some embodiments of the present disclosure. In some embodiments, a PET-MRI scan may include a PET scan and an MR scan. In some embodiments, the processing device 120 may cause an acquisition curve (e.g., D1 in FIG. 5C, D2 in FIG. 5D, and D3 in FIG. 5E) to be displayed in an interactive interface (e.g., the interactive interface 900 in FIG. 5C, the interactive interface 1000 in FIG. 5D, and the interactive interface 1110 in FIG. 5E). The acquisition curve may be displayed in a coordinate system (e.g., H1 in FIG. 5C, H2 in FIG. 5D, and H3 in FIG. 5E). A horizontal axis of the coordinate system may denote acquisition time of a PET-MRI scan and be labeled by, e.g., "Time/s." A vertical axis of the coordinate system may denote a count rate of the PET scan and be labeled by, e.g., "Count Rate/kcps." In some embodiments, there may be a displaying window (e.g., C1 in FIG. 5C, C2 in FIG. 5D, and C3 in FIG. 5E) configured to display the acquisition curve in the interactive interface. In the displaying window, at least a portion of the acquisition curve may be displayed.

In some embodiments, one or more second acquisition time periods corresponding to one or more scan sequences performed in the MR scan may be displayed in the interactive interface. The one or more second acquisition time periods may be displayed in the coordinate system. Merely by way of example, the one or more second acquisition time periods may be represented by one or more rectangular boxes. The one or more second acquisition time periods may be displayed corresponding to the horizontal axis of the coordinate system to present the time correspondence between the MR scan and the PET scan. For example, as shown in FIGS. 5C-5E, a GRE sequence, a FSE sequence, a DWI sequence, a BOLD1 sequence, and a BOLD2 sequence may be performed in the MR scan in sequence. The corresponding second acquisition time periods may be displayed in the form of rectangular boxes (e.g., E1 in FIG. 5C, E2 in FIG. 5D, and E3 in FIG. 5E) labeled by GRE, FSE, DWI, BOLD1, and BOLD2, respectively. The width of a rectangular box along the horizontal axis of the coordinate system may represent the duration of the corresponding second acquisition time period. The horizontal coordinates, on the horizontal axis, of two vertical sides (e.g., the left side and the right side) of a rectangular box may denote a start point and an end point of the corresponding scan sequence. In some embodiments, a vertical side of a rectangular box may be highlighted. For example, as shown in FIG. 5C, a pointer 903 may be displayed to indicate a vertical side of a rectangular box corresponding to a second acquisition time period of the BOLD2 sequence. As another example, a vertical side of a rectangular box may be displayed in a different color from a horizontal side of the rectangular box.

In some embodiments, one or more interaction identifiers may be displayed in the interactive interface. The first acquisition time period may be determine by controlling a state of the one or more interaction identifiers (e.g., the size of the one or more interaction identifiers and/or the position of the one or more interaction identifiers in the coordinate system). For example, the one or more interaction identifiers may include a rectangular frame (e.g., the rectangular frame 901 in FIG. 5C, the rectangular frame 1001 in FIG. 5D, and the rectangular frame 1101 in FIG. 5E). The two sides of the rectangular frame that are vertical to the horizontal axis may be adjusted to determine a start point, an end point, and the duration of a first acquisition time period. The width of the rectangular frame along the horizontal axis of the coordinate system may represent the duration of the first acquisition time period. The horizontal coordinates, on the horizontal axis, of the two vertical sides of the rectangular frame may denote the start point and the end point of the first acquisition time period. In some embodiments, when a mouse is placed in an interaction identifier, information (e.g., 1103 in FIG. 5E) of the corresponding imaging data set may be displayed. For example, as shown in FIG. 5E, when a mouse is placed in the interaction identifier 1101, a period time 30 s in which the corresponding imaging data set is acquired and the data quantity 600 Mcps of the corresponding imaging data set may be displayed. In some embodiments, multiple interaction identifiers may be displayed simultaneously in the interactive interface.

In some embodiments, the rectangular frame may be moved as a whole in the coordinate system. In some embodiments, a vertical line of the rectangular frame may be moved individually in the coordinate system. For example, when a user puts a mouse on a vertical line of the rectangular frame, an adjustment identifier (e.g., F1 in FIG. 5D) may be displayed. The vertical line may be individually moved by dragging the adjustment identifier. As another example, a horizontal coordinate (e.g., 1104 in FIG. 5E) of the vertical line may be displayed with the adjustment identifier. When the adjustment identifier is being dragged to adjust the position of the vertical line in the coordinate system, the horizontal coordinate of the vertical line may be updated synchronous with the real-time variation of the position of the vertical line.

In some embodiments, when a vertical line of the rectangular frame is being moved to determine the first acquisition time period, the processing device 120 may determine whether a difference between a real-time horizontal coordinate of the vertical line and a horizontal coordinate of a start point (or an end point) of a scan sequence is less than a threshold. In response to determining that the difference is less than the threshold, the processing device 120 may automatically adjust the vertical line to be consistent with the start point (or the end point) of the scan sequence. In some embodiments, when a vertical line of the rectangular frame is positioned consistent with a start point (or an end point) of a scan sequence along the horizontal axis, an indicator may be displayed to indicate that the vertical line is now positioned consistent with a start point (or an end point) of a scan sequence along the horizontal axis. For example, the vertical line may be changed to green color.

In some embodiments, according to operation 530 of the process 500, after a start point and/or an end point of a first acquisition time period is determined by controlling an interaction identifier to a first state (e.g., 904 in FIG. 5C), the processing device 120 may automatically adjust the determined start point and/or end point to be consistent with a start point and/or an end point of an MR scan sequence (e.g., the rectangular box labeled with "BOLD1" in FIG. 5C). The process that the interaction identifier is automatically changed from the first state indicating the first acquisition time period to a second state (e.g., 901 in FIG. 5C) indicating a third acquisition time period may be displayed in the interactive interface.

In some embodiments, a reconstruction parameter list (e.g., B1 in FIG. 5C, B2 in FIG. 5D, and B3 in FIG. 5E) may be displayed in the interactive interface. A row of the reconstruction parameter list may include a parameter group corresponding to a third acquisition time period. A parameter group may include one or more reconstruction parameters (e.g., the duration, the start time, or the end time of the corresponding third acquisition time period, a frame count, a frame time, or the quantity of the corresponding imaging data set), a sequence number, an option as to whether to reconstruct the corresponding imaging data set, or the like, or any combination thereof. For example, the user may determine to reconstruct the imaging data set by, e.g., selecting a symbol of "✓."

In some embodiments, after one or more third acquisition time periods are determined, the parameter group corresponding to at least one of the determined one or more third acquisition time periods may be added into the reconstruction parameter list. In some embodiments, the user may input and/or modify the one or more reconstruction parameters (e.g., the frame count, the frame time, and/or the duration of the third acquisition time period) in the reconstruction parameter list. For example, a user may perform a dragging operation or use the mouse wheel to adjust the one or more reconstruction parameters, thereby simplifying the adjustment and/or input of the one or more reconstruction parameters. In some embodiments, when one or more parameter groups in the reconstruction parameter list is selected (e.g., the gray highlighted Group No. 3 in FIG. 5C, the gray highlighted Group No. 4 in FIG. 5D, or the gray highlighted Group No. 4 in FIG. 5E), the interaction identifier indicating the corresponding third acquisition time period may be displayed in the displaying window.

In some embodiments, one or more buttons (e.g., A1 in FIG. 5C, A2 in FIG. 5D, and A3 in FIG. 5E) such as a share button, an adding button, a deletion button, a saving button, an export button, an import button, a zooming button, etc. may be displayed in the interactive interface. The share button may be configured to cause one or more parameter groups in the reconstruction parameter list to be shared with an external device (e.g., a terminal device associated with the user). The adding button may be configured to cause one or more parameter groups to be added into the reconstruction parameter list. The deletion button may be configured to cause one or more parameter groups to be deleted from the reconstruction parameter list. The saving button may be configured to cause one or more parameter groups to be saved in a storage device (e.g., the storage device 130, the storage 220 of the processing device 120, the storage unit 370 of the terminal 140, the memory of the terminal 140, an external storage device, etc.). The export button may be configured to cause one or more parameter groups to be exported. The import button may be configured to cause one or more reconstruction parameters to be obtained. The zooming button may be configured to cause at least a portion of the acquisition curve to be zoomed in or zoomed out in the displaying window.

In some embodiments, a reconstruction button (e.g., 902 in FIG. 5C, 1002 in FIG. 5D, and 1102 in FIG. 5E) configured to cause one or more imaging data sets to be reconstructed may be displayed in the interactive interface. For example, when one or more parameter groups are selected to be reconstructed (e.g., labeled with "✓") in the reconstruction parameter list, the reconstruction button may cause the one or more imaging data sets corresponding to the one or more selected parameter groups to be reconstructed.

In some embodiments, information (e.g., G1 in FIG. 5C and G3 in FIG. 5E) related to the duration of the PET scan and/or the time for reconstruction of one or more parameter groups that are selected to be reconstructed in the reconstruction parameter list may be displayed on the interactive interface.

According to the interactive interface, the acquisition curve and coordinates thereof may be displayed such that the user can observe a temporal variation of first modality data (e.g., PET data) and determine a reconstruction range based on the temporal variation of the first modality data. A visualization of the acquisition curve and coordinates thereof, and the one or more second acquisition time periods may be achieved, such that the user can have a clear understanding of the comparison between the process of the scan of the first modality and the process of the scan of the second modality. The user may determine the first acquisition time period using the one or more second acquisition time periods for reference, thereby making the first acquisition time period more similar to at least one of the one or more second acquisition time period.

Figure 6:
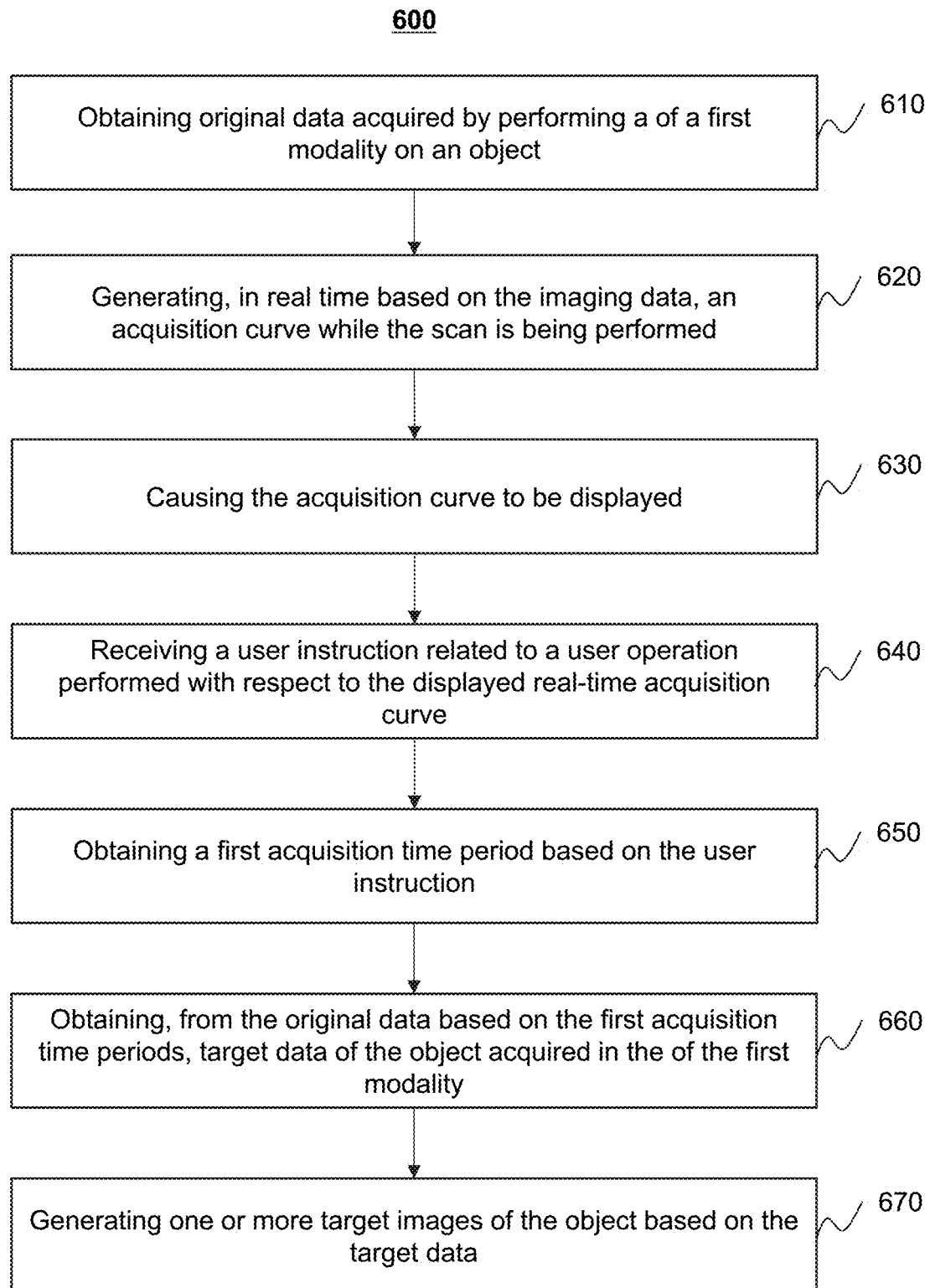
FIG. 6 is a flowchart illustrating an exemplary process for image reconstruction according to some embodiments of the present disclosure.

FIG. 6 is a flowchart illustrating an exemplary process for image reconstruction according to some embodiments of the present disclosure. In some embodiments, process 600 may be implemented as a set of instructions (e.g., an application) stored in a storage device (e.g., the storage device 130 and/or the storage 220 of the processing device 120). The processing device 120 (e.g., the processor 210 and/or one or more modules illustrated in FIG. 4) may execute the set of instructions, and when executing the instructions, the processing device 120 may be configured to perform the process 600. The operations of the illustrated process presented below are intended to be illustrative. In some embodiments, the process 600 may be applied to a single-modality scan (e.g., a PET scan or an SPECT scan) or a multi-modality scan (e.g., a PET-MRI scan, an SPECT-MRI scan, a PET-CT scan, or an SPECT-CT scan) performed by an imaging device (e.g., the imaging device 110).

In 610, the processing device 120 (e.g., the data obtaining module 420) may obtain original data acquired by performing a scan (e.g., a PET scan or an SPECT scan) on an object. In some embodiments, the scan may be a single-modality scan or a portion of a multi-modality scan. In some embodiments, the processing device 120 may obtain the original data directly from the imaging device 110 or from a storage device (e.g., the storage device 130, the storage 220 of the processing device 120, etc.).

In 620, the processing device 120 (e.g., the time obtaining module 410) may generate, in real time based on the original data (e.g., PET data or SPECT data), an acquisition curve while the scan is being performed.

In some embodiments, the acquisition curve may reflect a temporal variation of the original data acquired during the scan. For example, the acquisition curve may reflect a temporal variation of a count rate of the original data acquired in the scan. The count rate may refer to a count of gamma protons that are generated based on the tracer, emit from the object, and are detected by the imaging device 110. The horizontal axis of the acquisition time period may denote the time of the scan. The vertical axis of the acquisition time period may denote the count rate of the original data.

In some embodiments, the processing device 120 may determine, based on the original data, a count rate of the original data. The processing device 120 may determine the acquisition curve based on the count rate of the original data. In some embodiments, during the scan, the imaging device 110 may continuously acquire the original data in real time. The processing device 120 may update the acquisition curve based on the real-time updated original data.

In 630, the processing device 120 (e.g., the time obtaining module 410) may cause the acquisition curve to be displayed.

In some embodiments, the acquisition curve updated in real time may be displayed on an interactive interface through, e.g., the I/O 230 of the processing device 120, and/or the I/O 350 and/or the display unit 320 of the terminal 140, so that the process that the acquisition curve develops from the start to the end of the scan may be presented to a user.

In some embodiments, the acquisition curve may be adaptively displayed on the interactive interface, such that the displayed acquisition curve may not be too small or too large in the interactive interface, thereby the user can observe the acquisition curve conveniently. For example, there may be a displaying window in the interactive interface for displaying the acquisition curve. The size of the acquisition curve may be adjusted in real time so that the size of the displayed acquisition curve fits the size of the displaying window. For instance, when the scan has been performed for 5 minutes, the acquisition curve may be displayed in a first size. When the scan has been performed for 6 minutes, the acquisition curve may be displayed in a second size smaller than the first size. As another example, the displaying window may be configured to display a fixed time range of the acquisition curve. The displayed portion of the acquisition curve may be adjusted in real time so that the lasted generated portion of the acquisition curve may be displayed in the displaying window. For instance, the displaying window may be configured to display a fixed time range of 100 s. When the scan has been performed for 120 seconds, a portion corresponding to 20-120 seconds of the acquisition curve may be displayed in the displaying window. When the scan has been performed for 200 seconds, a portion corresponding to 100-200 seconds of the acquisition curve may be displayed in the displaying window. In some embodiments, the displaying window may be configured to display at least a portion of the acquisition curve. When only a portion of the acquisition curve is displayed in the displaying window, a user may move the acquisition curve to cause other portion of the acquisition curve to be displayed in the displaying window.

In some embodiments, the injection time of the tracer into the object may be displayed in the interactive interface. For example, an injection line may be displayed on the acquisition curve. The injection line may be a line that is vertical to the horizontal axis of the acquisition curve and used to label the injection time of the tracer. A horizontal coordinate of the vertical line in the horizontal axis may refer to the injection time of the tracer. For instance, the vertical line may be intersected with the acquisition curve at a specific point. A horizontal coordinate of the specific point may denote the injection time and a vertical coordinate of the specific point may denote the count rate of the original data at the injection time. In some embodiments, the count rate and the injection time corresponding to the specific point may be displayed in the interactive interface. In some embodiments, the injection line may be displayed in a form different from that of the acquisition curve. For example, the injection line may be displayed in a color different from that of the acquisition curve. As another example, the injection line may be displayed in a dashed line, while the acquisition curve may be displayed in a solid line.

In 640, the processing device 120 (e.g., the time obtaining module 410) may receive a user instruction related to a user operation performed with respect to the real-time displayed acquisition curve.

In some embodiments, the user operation performed with respect to the real-time displayed acquisition curve may include specifying at least one of a start point of a first acquisition time period, an end point of the first acquisition time period, and the duration of the first acquisition time period.

In some embodiments, a start identifier and/or an end identifier (e.g., a vertical line, a box, a point, a cross, an arrow, etc.) may be displayed in the interactive interface. The start identifier and the end identifier may be differentially displayed to distinguish the start identifier and the end identifier. For example, the start identifier and the end identifier may be displayed with different colors, icons, labels, etc. The user operation may include moving the start identifier and/or the end identifier on the acquisition curve to determine at least one of the start point of the first time period, the end point of the first time period, and the duration of the first time period. For instance, a start line and an end line which are vertical to the horizontal axis may be displayed on the interactive interface. The start line and an end line may be moved (or dragged) on the acquisition curve along the horizontal axis. The user may determine the start point of the first acquisition time period by moving (or dragging) the start line to a first position on the acquisition curve and determine the end point of the first acquisition time period by moving (or dragging) the end line to a second position on the acquisition curve. The processing device 120 may receive the user instructions related to the moving operations.

In some embodiments, two identifiers may be displayed without distinguishing the start identifier and the end identifier. The user may move the two identifiers to two positions on the acquisition curve, respectively. The position corresponding to an earlier time point may be defined to be the start point of the first acquisition time period. The other position corresponding to a later time point may be defined to be the end point of the first acquisition time period.

In some embodiments, a rectangular frame may be displayed in the interactive interface. The two sides of the rectangular frame that are vertical to the horizontal axis of the acquisition curve may be referred to as the start identifier and the end identifier. The width along the horizontal axis of the acquisition curve may be referred to as the duration of the first acquisition time period. In some embodiments, the user may move the start identifier and the end identifier simultaneously by moving the rectangular frame as a whole. In some embodiments, the user may individually move the start identifier (or the end identifier) to adjust the duration of the first acquisition time period and the start point (or the end point) of the first acquisition time period.

In some embodiments, there may be no start identifier and end identifier that are displayed in the interactive interface.

For example, a user may click two positions on the acquisition curve. The horizontal coordinate of one of the two positions that corresponding to an earlier time point may be defined as the start point of the first acquisition time period. The horizontal coordinate of the other of the two positions that corresponding to a later time point may be defined as the end point of the first acquisition time period.

As another example, a user may click a first position on the acquisition curve, then perform dragging operation from the first position to a second position on the acquisition curve. The position, corresponding to an earlier time point, of the first position and the second position may be defined as the start point of the first acquisition time period. The other position, corresponding to a later time point, of the first position and the second position may be defined as the end point of the first acquisition time period. The trajectory of the dragging operation between the first and the second positions may be displayed in the interactive interface.

In 650, the processing device 120 (e.g., the time obtaining module 410) may obtain the first acquisition time period (also referred to as a reconstruction range) based on the user instruction. In some embodiments, descriptions regarding obtaining the first acquisition time period based on the user instruction in connection with operation 510 of the process 500 in FIG. 5A and FIGS. 5C-5E may be applied in the process 600.

In 660, the processing device 120 (e.g., the data obtaining module 420) may obtain, based on the first acquisition time periods, target data of the object acquired in the scan. In some embodiments, the target data of the object may be PET data or SPECT data acquired during the first acquisition time period in the scan. In some embodiments, the processing device 120 may obtain the target data from a storage device (e.g., the storage device 130, the storage 220 of the processing device 120, etc.) and/or the imaging device 110.

In 670, the processing device 120 (e.g., the reconstruction module 430) may generate one or more target images of the object based on the target data. Details regarding generating the one or more target images may be found elsewhere in the present disclosure (e.g., descriptions in connection with operation 550 of the process 500 in FIG. 5A and FIG. 8).

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process presented below are intended to be illustrative.

Figure 7A:
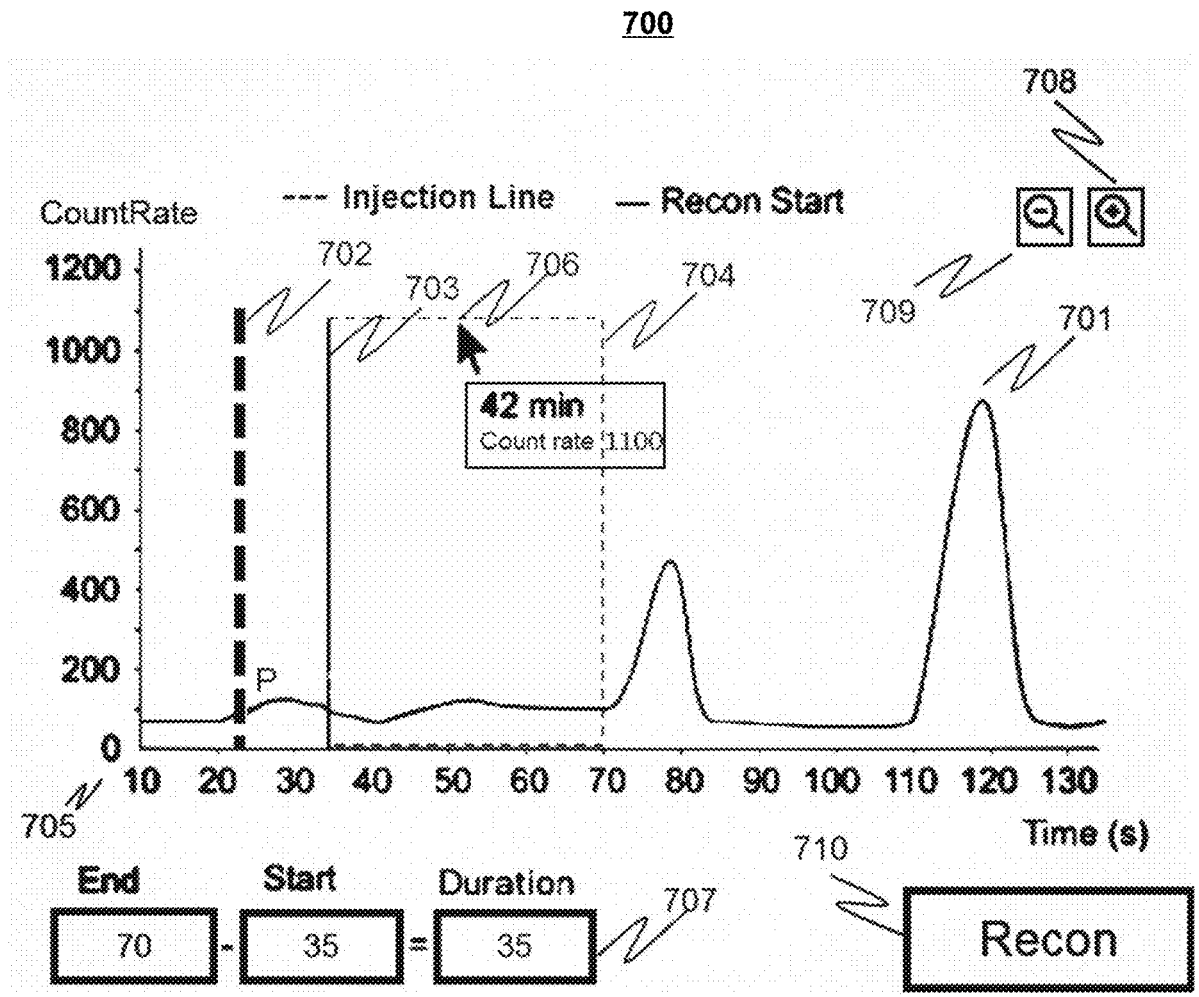
FIG. 7A is a schematic diagram illustrating an exemplary interactive interface according to some embodiments of the present disclosure.

FIG. 7A is a schematic diagram illustrating an exemplary interactive interface according to some embodiments of the present disclosure. In some embodiments, a coordinate system 705 may be displayed in the interactive interface 700. A horizontal axis of the coordinate system 705 may denote the time of a scan (e.g., a PET scan or an SPECT scan) and be labeled by, e.g., "Time (s)." A vertical axis of the coordinate system 705 may denote a count rate of original data (e.g., PET data or SPECT data) acquired during the scan and be labeled by, e.g., "CountRate." In some embodiments, when a mouse is positioned at any position in the coordinate system 705, coordinates of the position may be displayed in the interactive interface 700. For example, as shown in FIG. 7A, when a mouse is positioned at position 706 in the coordinate system 705, coordinates including 42 min and count rate 1100 of the position 706 may be displayed in the interactive interface 700.

In some embodiments, an acquisition curve 701 updated based on the original data updated in real-time may be displayed in the interactive interface 700. The process that the acquisition curve 701 develops from the start to the end of the scan may be presented in the interactive interface 700 in real-time.

In some embodiments, an injection line 702 may be displayed in the interactive interface 700. The injection line 702 may be intersected with the acquisition curve 701 at an intersection point P.

In some embodiments, a start identifier 703 may be displayed in the interactive interface 700. The start identifier 703 may be moved along the horizontal axis to determine a start time point of a first acquisition time point (also referred to as a reconstruction range). When the start time point of the first acquisition time point is determined by the start identifier 703, a user may perform a dragging operation from the start identifier 703 for a specific distance. The horizontal coordinate of the end of the dragging operation may be determined as the end time point of the first acquisition time point. In some embodiments, a trajectory (e.g., within the dashed frame 704) of the dragging operation may be displayed in the interactive interface 700.

In some embodiments, an input box 707 configured to input and/or display a value of the start time point, a value of the end time point, and a value of the duration of the first acquisition time may be displayed in the interactive interface 700. The input box 707 may include a box labeled with "Start" configured to input and/or display a value of the start time point of the first acquisition time, a box labeled with "End" configured to input and/or display a value of the end time point of the first acquisition time, and a box labeled with "Duration" configured to input and/or display a value of the duration of the first acquisition time.

In some embodiments, after a user determines the first acquisition time period on the acquisition curve 701 through the start identifier 703, information of the determined first acquisition time period may be displayed in the input box 707. For example, the user may move the start identifier 703 to the position of 35 s on the horizontal axis. Then, the user may perform a dragging operation from the start identifier 703 to make a trajectory 704 to determine an end time point of 70 s. Then, as shown in FIG. 7A, the input box 707 may display "70−35=35," indicating that the start time point of the first acquisition time period is 35 s, the end time point of the first acquisition time period is 70 s, and the duration of the first acquisition time period is 35 s.

In some embodiments, when the start identifier 703 is being moved along the horizontal axis, the value displayed in the "Start" box of the input box 707 may be changed synchronous with the variation of the real-time position of the start identifier 703 on the horizontal axis. In some embodiments, the position of the start identifier 703 on the horizontal axis may be adjusted by changing the value in the "Start" box of the input box 707.

In some embodiments, one or more function buttons (e.g., buttons 708-710) may be displayed in the interactive interface 700. The button 708 may be configured to cause at least a portion of the acquisition curve 701 to be zoomed in. The button 709 may be configured to cause at least a portion of the acquisition curve 701 to be zoomed out. In some embodiments, the buttons 708 and 709 may cause at least a portion of the acquisition curve 701 to be zoomed in and zoomed out according to a preset percentage (e.g., 5%, 10%, 15%, etc.). Taking the preset percentage of 5% as an example, a user may specify a specific portion of the acquisition curve 701 and click the button 708. After a first click of the button 708, the specific portion of the acquisition curve 701 may be zoomed in by 5%. After a second click of the button 708, the zoomed-in specific portion of the acquisition curve 701 may continue to be zoomed in by 5%. In some embodiments, when the button 708 or 709 is clicked, a scaling ratio of the acquisition curve 701 may be displayed on the interactive interface 700. Taking the preset percentage of 5% as an example, if the button 708 is clicked once, the specific portion of the acquisition curve 701 may be zoomed in by 5% and the scaling ratio may be displayed to be 105% in the interactive interface 700. The button 710 may be configured to cause a reconstruction operation to be performed. When the button 710 is clicked, target data (e.g., PET or SPECT data) acquired in the first acquisition time period may be obtained and be reconstructed.

In some embodiments, the interactive interface 700 may be displayed with other information. For example, the reconstruction parameter list and/or the buttons illustrated in FIGS. 5C-5E may be displayed in the interactive interface 700.

Figure 7B:
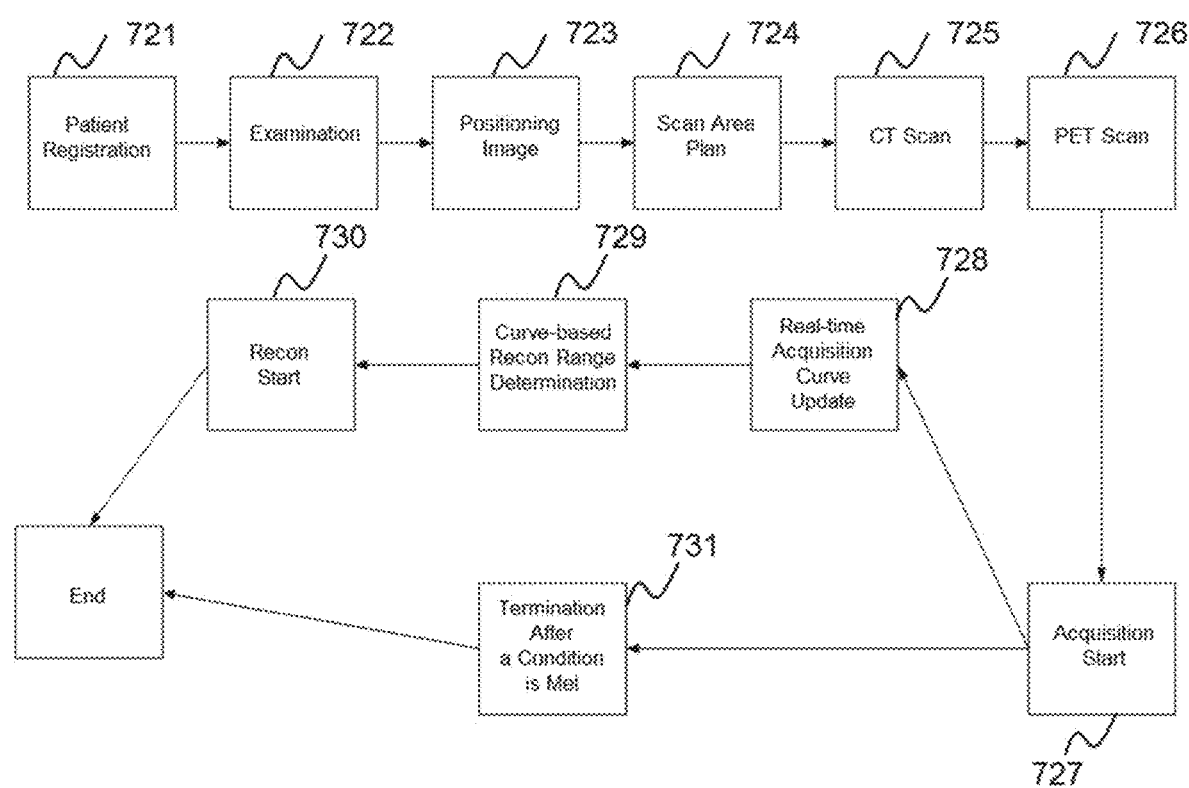
FIG. 7B is a schematic diagram illustrating an exemplary workflow of a PET-CT scan according to some embodiments of the present disclosure.

FIG. 7B is a schematic diagram illustrating an exemplary workflow of a PET-CT scan according to some embodiments of the present disclosure.

As shown in FIG. 7B, in 721, when a patient is determined to need a PET-CT scan according to a doctor's diagnosis, information (e.g., name, age, gender, disease, the purpose of the PET-CT, medical history, etc.) of the patient may be registered to the imaging system 100. In 722, after the patient registration, an examination may be performed on the patient to determine the patient is suitable to receive the PET-CT scan. In 723, a pre-scan may be performed on the patient to obtain a positioning image which is used to plane a scan region in the subsequent formal scan. In 724, a region of interest (ROI) of the patient to be scanned may be determined. In 725, the imaging device 110 may perform a CT scan on the ROI of the patient. In 726 and 727, the imaging device 110 may start to perform a PET scan on the ROI of the patient after the CT scan. In 728, during the PET scan, an acquisition curve may be generated according to PET data acquired in real-time using operation 620 of the process 600 in FIG. 6. The real-time acquisition curve may be displayed on an interactive interface. In 729, a user may determine a reconstruction range when the PET scan is being performed. For example, the reconstruction range may be determined according to a user instruction performed with respect to the real-time acquisition curve (e.g., selecting a target range on the displayed acquisition curve through the interactive interface). In 730, PET data acquired during the determined reconstruction range may be reconstructed to generate one or more PET images. In 731, when a termination condition is met, the PET scan may be terminated. Exemplary termination condition may include the PET scan has been performed for a preset time period (e.g., 10 minutes, 20 minutes, etc.).

Figure 8:
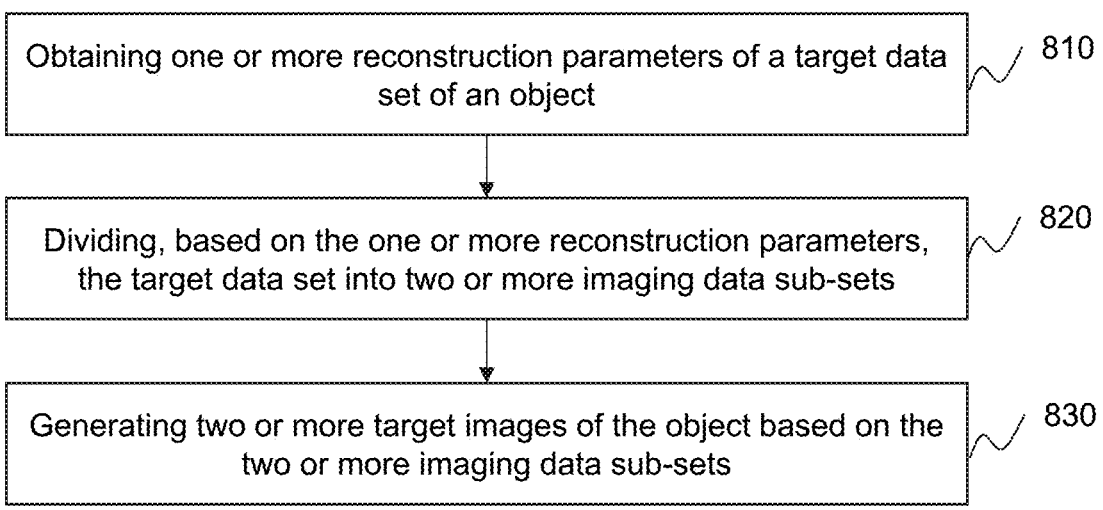
FIG. 8 is a flowchart illustrating an exemplary process for dynamic reconstruction according to some embodiments of the present disclosure.

FIG. 8 is a flowchart illustrating an exemplary process for dynamic reconstruction according to some embodiments of the present disclosure. In some embodiments, process 800 may be implemented as a set of instructions (e.g., an application) stored in a storage device (e.g., the storage device 130 and/or the storage 220 of the processing device 120). The processing device 120 (e.g., the processor 210 and/or one or more modules illustrated in FIG. 4) may execute the set of instructions, and when executing the instructions, the processing device 120 may be configured to perform the process 8500. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, operation 550 of the process 500 in FIG. 5A and/or operation 670 of the process 600 in FIG. 6 may be performed based on the process 800. In some embodiments, the process 800 may be described in connection with dynamic reconstruction to generate two or more target images.

In 810, the processing device 120 (e.g., the reconstruction module 430) may obtain one or more reconstruction parameters of a target data set of an object. In some embodiments, the target data set may include PET data or SPECT data. In some embodiments, the target data set may be an imaging data set acquired in a third acquisition time period illustrated in the process 500 in FIG. 5A. In some embodiments, the target data set may be the target data acquired in the first acquisition time period illustrated in the process 600 in FIG. 6.

In some embodiments, the one or more reconstruction parameters may include frame configuration information (e.g., a frame count and a frame time) of the target data set and an acquisition time (e.g., the first acquisition time period or the third acquisition time period) in which the target data set is acquired.

In some embodiments, the processing device 120 may determine the frame configuration information based on a user instruction. For example, the user may manually input the frame count and the frame time. As another example, the user may manually input the frame count. The processing device 120 may determine the frame time based on the frame count and the acquisition time period, e.g., by dividing the acquisition time period by the frame count. As still another example, the user may manually input the frame time. The processing device 120 may determine the frame count based on the frame time and the acquisition time period, e.g., by dividing the acquisition time period by the frame time.

In some embodiments, a plurality of candidate frame count values and candidate frame time values may be stored in a storage device (e.g., the storage device 130, the storage 220 of the processing device 120, the storage unit 370 of the terminal 140, the memory 360 of the terminal, an external storage device, etc.). The user may import a candidate frame count value and/or a candidate frame time value from the storage device. In some embodiments, the processing device 120 may use the candidate frame count value and/or the candidate frame time value to perform the dynamic reconstruction. In some embodiments, the user may adjust the candidate frame count value and/or the candidate frame time value. The processing device 120 may use the modified candidate frame count value and/or the modified candidate frame time value to perform the dynamic reconstruction.

In some embodiments, the user instruction may be generated based on a user operation performed on an interactive interface of the imaging system 100 through, e.g., the I/O 230 of the processing device 120, and/or the display unit 320 and/or the I/O 350 of the terminal 140.

In some embodiments, the processing device 120 may determine the frame count and/or the frame time based on a time resolution of the imaging device 110. The time resolution may indicate a capacity of the imaging device 110 to detect photons emitted from the object. For example, the time resolution may indicate the maximum number (or count) of photons the imaging device 110 can detect per unit time (e.g., per second, per minute, etc.).

In some embodiments, the processing device 120 may determine the frame configuration information based on, e.g., the duration of the PET or SPECT scan, the position of the object in the detection region of the imaging device 110, the type and concentrate of the tracer, the type of the object, the purpose of scanning the object, the scan protocol used to scan the object, a reconstruction algorithm, the duration of the acquisition time period, or the like, or any combination thereof.

In some embodiments, the processing device 120 may export and store the one or more determined reconstruction parameters (e.g., the reconstruction range, the frame count, and/or the frame time). The one or more reconstruction parameters may be stored in a storage device (e.g., the storage device 130, the storage 220 of the processing device 120, the storage unit 370 of the terminal 140, the memory 360 of the terminal 140, or an external storage device). In some embodiments, the one or more reconstruction parameters may be stored in a common data format such as a Comma-Separated Values (CSV) format, a JavaScript Object Notation (JSON) format, or a text file (txt) format. The stored reconstruction parameters may be retrieved by the user subsequently, avoiding re-setting the reconstruction parameters in same or similar reconstruction tasks, thereby simplifying the determination and/or input of the reconstruction parameters (e.g., the reconstruction range, the frame count, and/or the frame time).

In some embodiments, the processing device 120 may store the one or more reconstruction parameters with one or more keywords which can improve the utilization, retrieval, and identification of the one or more reconstruction parameters. The one or more keywords may include, for example, the type of the scan performed on the object, the duration of a multi-modality scan, the duration of a scan of a first modality in the multi-modality scan, the duration of a scan of a second modality in the multi-modality scan, the type and concentration of the tracer, the types of one or more scan sequences, the order of performing the one or more scan sequences, the position of the object in the detection region of the imaging device 110, the type of the object, the purpose of scanning the object, the scan protocol used to scan the object, or the like, or any combination thereof.

Merely by way of example, in a first reconstruction task, the imaging device 110 may perform a first PET-MRI scan including a first MR scan and a first PET scan. The imaging device 110 may perform a T1WI sequence, a T2WI sequence, and a DWI sequence in sequence in the first MR scan. The processing device 120 may store the reconstruction parameters used to perform dynamic PET reconstruction corresponding to the first PET scan with keywords of the T1WI sequence, the T2WI sequence, and the DWI sequence, and the performing order thereof. In a second reconstruction task subsequent to the first reconstruction task, the imaging device 110 may perform a second PET-MRI scan including a second MR scan and a second PET scan. The imaging device 110 may perform a T1WI sequence, a T2WI sequence, and a DWI sequence in sequence in the second MR scan. When performing dynamic PET reconstruction corresponding to the second PET scan, the processing device 120 may identify the stored reconstruction parameters of the first reconstruction task as a PET reconstruction range and/or frame configuration information of the second reconstruction task by retrieving the keywords of the T1WI sequence, the T2WI sequence, and the DWI sequence, and the performing order thereof.

In some embodiments, a user may input one or more keywords in an interactive interface (e.g., the interactive interface illustrated in FIG. 5C, 5D, 5E, or 7A). The processing device 120 may import, from the stored parameters, one or more reconstruction parameters (e.g., an acquisition time period, a frame count, and/or a frame time) based on the input keywords.

In some embodiments, the function of exporting and/or storing a template of one or more reconstruction parameters illustrated in operation 810 may be applied to a single-modality scan (e.g., a PET scan or an SPECT scan) or a multi-modality scan (e.g., a PET-MRI scan, an SPECT-MRI scan, a PET-CT scan, or an SPECT-CT scan).

In 820, the processing device 120 (e.g., the reconstruction module 430) may divide, based on the one or more reconstruction parameters, the target data set into two or more imaging data sub-sets. In some embodiments, a count of the one or more imaging data sub-sets may be the same as the determined frame count. Each of the two or more imaging data sub-sets may be acquired during a time period equal to the determined frame time.

In 830, the processing device 120 (e.g., the reconstruction module 430) may generate two or more target images of the object based on the two or more imaging data sub-sets. In some embodiments, a target image may be a PET image or an SPECT image. In some embodiments, the processing device 120 may generate each of the two or more target images by performing PET or SPECT reconstruction on one of the two or more imaging data sub-sets.

It should be noted that the above descriptions regarding the processes 800 and 900 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting.

Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device including a set of instructions; and
   at least one processor configured to communicate with the at least one storage device, wherein when executing the set of instructions, the at least one processor is configured to direct the system to perform operations including:
      obtaining a first acquisition time period related to a scan of a first modality performed on an object;
      obtaining one or more second acquisition time periods related to a scan of a second modality performed on the object;
      obtaining, based on the first acquisition time period and the one or more second acquisition time periods, target data of the object acquired in the scan of the first modality; and
      generating one or more target images of the object based on the target data.

2. The system of claim 1, wherein obtaining, based on the first acquisition time period and the one or more second acquisition time periods, the target data of the object acquired in the scan of the first modality includes:
   determining one or more third acquisition time periods based on the first acquisition time period and the one or more second acquisition time periods, each of the one or more third acquisition time periods being consistent with one of the one or more second acquisition time periods; and
   obtaining the target data acquired during the one or more third acquisition time periods in the scan of the first modality.

3. The system of claim 2, wherein when executing the set of instructions, the at least one processor is configured to direct the system to perform the operations including:
   causing at least one of the first acquisition time period, the one or more second acquisition time periods, or the one or more third acquisition time periods to be displayed.

4. The system of claim 2, wherein when executing the set of instructions, the at least one processor is configured to direct the system to perform operations including:
   storing the one or more third acquisition time periods.

5. The system of claim 1, wherein generating the one or more target images of the object based on the target data includes:
   obtaining one or more reconstruction parameters associated with the target data; and
   generating, based on the target data and the one or more reconstruction parameters, the one or more target images of the object.

6. The system of claim 5, wherein the one or more reconstruction parameters include at least one of a count of the one or more target images or a frame time of the one or more target images.

7. The system of claim 1, wherein when executing the set of instructions, the at least one processor is configured to direct the system to perform the operations including:
   generating, in real time based on original data having been acquired in the scan of the first modality, an acquisition curve while the scan of the first modality is being performed; and
   causing the acquisition curve to be displayed.

8. The system of claim 7, wherein the acquisition curve reflects a temporal variation of a count rate of the original data.

9. The system of claim 7, wherein the first acquisition time period is obtained based on the acquisition curve.

10. The system of claim 1, wherein the first modality is positron emission tomography (PET) or single photon emission computed tomography (SPECT), and the second modality is magnetic resonance (MR).

11. The system of claim 10, wherein one or more scan sequences are applied in the scan of the second modality.

12. The system of claim 11, wherein each of the one or more second acquisition time periods corresponds to one of the one or more scan sequences.

13. The system of claim 1, wherein at least a portion of the scan of the second modality is performed synchronously with at least a portion of the scan of the first modality.

14. The system of claim 1, wherein when executing the set of instructions, the at least one processor is configured to direct the system to perform the operations including:
   obtaining second modality data acquired in at least one of the one or more second acquisition time periods of the scan of the second modality, the at least one of the one or more second acquisition time periods relating to the first acquisition time period;
   generating one or more second modality images of the object based on the second modality data; and
   causing the one or more target images and the one or more second modality images to be displayed in fusion.

15. A system, comprising:
   at least one storage device including a set of instructions; and
   at least one processor configured to communicate with the at least one storage device, wherein when executing the set of instructions, the at least one processor is configured to direct the system to perform operations including:
      obtaining original data acquired by performing a scan on an object;
      generating, in real time based on the original data, an acquisition curve while the scan is being performed;
      obtaining a reconstruction range based on the acquisition curve;
      obtaining, from the original data, target data based on the reconstruction range; and
      generating one or more target images of the object based on the target data.

16. The system of claim 15, wherein the acquisition curve reflects a temporal variation of a count rate of the original data.

17. The system of claim 15, wherein when executing the set of instructions, the at least one processor is configured to direct the system to perform the operations including:
   causing the acquisition curve to be displayed.

18. The system of claim 17, wherein obtaining the reconstruction range based on the acquisition curve includes:
   receiving a user instruction related to a user operation performed with respect to the displayed acquisition curve; and
   obtaining the reconstruction range based on the user instruction.

19. The system of claim 15, wherein when executing the set of instructions, the at least one processor is configured to direct the system to perform operations including:

causing to be displayed an injection time of a radioactive tracer into the object.

20. A method implemented on a machine include one or more processors and one or more storage devices, comprising:

obtaining a first acquisition time period related to a scan of a first modality performed on an object;

obtaining one or more second acquisition time periods related to a scan of a second modality performed on the object;

obtaining, based on the first acquisition time period and the one or more second acquisition time periods, target data of the object acquired in the scan of the first modality; and generating one or more target images of the object based on the target data.

\* \* \* \* \*